(12) United States Patent
Brines et al.

(10) Patent No.: US 6,569,152 B2
(45) Date of Patent: May 27, 2003

(54) SUSTAINED RELEASE DELIVERY SYSTEMS FOR SOLUTES

(75) Inventors: Michael Brines, Woodbridge, CT (US); Anthony Cerami, Sleepy Hollow, NY (US); Jean-Paul Wuerth, Quogue, NY (US)

(73) Assignee: Farrington Pharmaceuticals, LLC, Tarrytown, NY (US)

( * ) Notice: Subject to any disclaimer, the term of this patent is extended or adjusted under 35 U.S.C. 154(b) by 8 days.

(21) Appl. No.: 09/798,777

(22) Filed: Mar. 2, 2001

(65) Prior Publication Data

US 2001/0039414 A1 Nov. 8, 2001

Related U.S. Application Data

(60) Provisional application No. 60/221,070, filed on Jul. 27, 2000, and provisional application No. 60/190,878, filed on Mar. 21, 2000.

(51) Int. Cl.⁷ .............. A61K 9/22; A61K 9/24; A61F 13/00
(52) U.S. Cl. .............. 604/890.1; 604/892.1; 424/422; 424/472
(58) Field of Search .............. 604/890.1, 892.1; 424/472, 464, 465, 434, 435, 436, 422, 427

(56) References Cited

U.S. PATENT DOCUMENTS

| 3,113,076 | A |   | 12/1963 | Jacobs |
|---|---|---|---|---|
| 3,146,169 | A |   | 8/1964 | Stephenson et al. |
| 3,851,648 | A |   | 12/1974 | Brooke |
| 3,924,622 | A |   | 12/1975 | Brooke |
| 3,987,790 | A |   | 10/1976 | Eckenhoff et al. |
| 4,160,452 | A | * | 7/1979 | Theeuwes .............. 128/260 |
| 4,357,312 | A |   | 11/1982 | Hsieh et al. |
| 4,601,893 | A |   | 7/1986 | Cardinal |
| 4,663,147 | A |   | 5/1987 | DePrince |
| 4,732,155 | A |   | 3/1988 | Zetter et al. |
| 4,803,076 | A |   | 2/1989 | Ranade |
| 4,816,262 | A |   | 3/1989 | McMullen |
| 4,872,873 | A |   | 10/1989 | Zingerman |
| 5,004,614 | A |   | 4/1991 | Staniforth |
| 5,342,627 | A |   | 8/1994 | Chopra et al. |
| 5,391,378 | A |   | 2/1995 | Sanderson |
| 5,618,560 | A |   | 4/1997 | Bar-Shalom |
| 5,633,000 | A | * | 5/1997 | Grossman et al. .......... 424/422 |
| 6,068,859 | A |   | 5/2000 | Curatolo et al. |

FOREIGN PATENT DOCUMENTS

| EP | 259 113 | 8/1928 |
|---|---|---|
| EP | 334 306 | 9/1989 |
| GB | 15161 | 7/2002 |

OTHER PUBLICATIONS

Kuu, Wei–Youh and Yalkowsky, Samuel H.; 1985, Multiple–Hole Approach to Zero–Order Release, Journal of Pharmaceutical Sciences, 74 (No. 9):926–933.

Dean S.T. Hsieh, William D. Rhine & Robert Langer; 5/81, Zero–Order Controlled–Release Polymer Matrices for Micro—and Macromolecules, Journal of Pharmaceutical Sciences, vol. 72, No. 1, 1/83.

* cited by examiner

Primary Examiner—Gregory L. Huson
Assistant Examiner—Anuradha Ramana
(74) Attorney, Agent, or Firm—Klauber & Jackson

(57) ABSTRACT

The present invention relates to devices that allow for linear, sustained-release of solutes with adjustable initial-release kinetics. In particular, the present invention relates to devices for delivering substances to the body of an animal. The present invention also relates to methods for delivering solutes in a constant, sustained-release fashion using the devices of the invention.

29 Claims, 25 Drawing Sheets

ı no gradient forming element
᠈ 1:3 gradient forming element
ᴇ 1:7 gradient forming element
  1:15 gradient forming element → cone without gradient forming element
-◆- cone with 1:3 gradient forming element
--■-- cone with 1:15 gradient forming element ——— uncoated frustoconical solute reservoir
- - - - coated frustoconical solute reservoir without gradient forming element
······ coated frustoconical solute reservoir with 1 mm gradient forming element
— — — coated frustoconical solute reservoir with 3 mm gradient forming element chloroquine release from multiple devices grouped

- 1 device
- 3 devices with release orifices 6 radii apart
- □ 6 devices with release orifices 4 radii apart
- ▼ 9 devices with release orifices 2 radii apart
- ♦ 12 devices with release orifices 1 radii apart
- ○ release from matrix alone

SUSTAINED RELEASE DELIVERY SYSTEMS FOR SOLUTES

CROSS-REFERENCE TO RELATED APPLICATIONS

This application claims priority to provisional application Ser. No. 60/190,878, filed Mar. 21, 2000, and No. 60/221,070, filed Jul. 27, 2000, both of which are incorporated herein by reference in their entireties.

FIELD OF THE INVENTION

The present invention relates to delivery systems that allow for sustained release of one or more solutes. In particular, the present invention relates to devices for delivering substances to the body of an animal or into other environments requiring a constant delivery and to methods of delivering these substances in a constant, sustained-release fashion.

BACKGROUND OF THE INVENTION

Drug delivery classically has been via oral dosage forms that release the drug as they dissolve in the gastrointestinal tract. These delivery systems typically provide for rapid release of the active substance, which leads to the presence of maximal concentrations of the drug in the blood followed by a rapid decrease in concentration as the drug is metabolized and cleared. At these maximal concentrations, many drugs are highly toxic. Furthermore, if the concentration decreases rapidly in the body, then the time during which there is a therapeutically-effective level is short, and therapeutic efficacy requires administration of multiple doses. In addition, if release of a substance in the body cannot be controlled, then it may not be effectively delivered to the site of the body requiring treatment.

Other solutes also benefit from devices that allow for their sustained release. For example, dosing of swimming pools with chlorine or hot tubs with bromine as anti-microbial agents currently requires adding these substances to the water on a fairly regular basis. Furthermore, if the concentration is not controlled and becomes too high upon addition, then the water may not be safe or pleasant for bathers until the concentration stabilizes at lower values. Other uses for sustained-release delivery systems include, for example, delivery of food or insecticides to plants, delivery of vaccines, antibiotics, anti-parasitic agents, growth promotants or other drugs to livestock, delivery of sanitizing agents or perfumes to toilets or septic tanks, delivery antibiotics or other drugs to companion animals, delivery of dyes, bleaches or other substances in the processing of textiles, delivery of algicides to water towers or ponds, delivery of food to fish in aquaria or ponds, and delivery of any substance requiring constant delivery in an industrial manufacturing process.

Various sustained release delivery devices have been described, including those in which a solute is contained within an impermeable housing with one or more openings from which solute egresses by diffusion. Such devices purport to deliver solute at a constant (zero-order) rate; however, many deviate significantly from zero order or linear delivery. In addition, such devices often are limited in the amount of total dose deliverable, as well as by fixed parameters that make it difficult or impossible to adjust the delivery kinetics. A common feature of such prior art devices is that their release kinetics are characterized by an initial burst of solute release prior to a period of relatively constant rate of release, and the relatively constant rate of release often only crudely approximates zero order. For several reasons, such an initial burst is undesirable, as it temporarily delivers a dose in excess of the desired, effective dose, thus wasting solute, and moreover, may deliver an amount of solute which is toxic or otherwise damaging in the particular application. In addition, the initial release of a large amount of solute reduces the total amount of solute subsequently available for prolonged release by the device, thus shortening the duration of relative constant delivery, reducing its effective life and requiring more frequent replacement.

The devices and methods of the present invention overcome the disadvantages of current devices and methods for the delivery of solutes by providing for reliable and adjustable sustained release of solutes in aqueous and non-aqueous environments. In addition to exhibiting adjustable, nearly-constant release rates over suitably prolonged periods of time, the devices and methods of the invention provide for modulation or suppression of the aforementioned initial burst. The devices and methods of the invention may be applied to any of the prior-art devices relying on a fenestration or orifice and a fluid- and solute-impervious coating, to provide prolonged and near zero-order release.

Discussion or citation of a reference herein shall not be construed as an admission that such reference is prior art to the present invention.

SUMMARY OF THE INVENTION

In a first embodiment, the present invention relates to a device for the continuous, linear, sustained release of one or more solutes. The device comprises at least one dispenser, each dispenser comprising at least one solute reservoir element, the solute reservoir element defined by a fluid-impervious and solute-impervious wall and having at least one orifice therein referred to as a source element, each source element being in fluid registry with a gradient-forming element, the gradient-forming element having a release orifice. The gradient-forming element is provided for preventing unwanted initial burst and release of solute while promoting controlled, prolonged near-zero-order release.

The solute reservoir element may have a shape such as but not limited to a hemisphere, sphere, pyramid, cylinder, tetrahedron, parallelepiped, or polyhedron. A hemisphere- or pyramid-shaped solute reservoir element is preferred. A hemispherical solute reservoir element is most preferred. Preferably, the ratio of the radius of a hemisphere or portion thereof representing the maximum internal diffusion surface of the solute reservoir element, to the radius of the source element, is equal to or greater than about two, and more preferably, the ratio is greater than or equal to about five. Most preferably, the ratio is equal to or greater than about ten.

The source element is an opening or passageway between the solute reservoir element and the gradient-forming element. It preferably has a circular cross-section but is not so limiting, and may have any shape.

The gradient-forming element may have a shape such as but not limited to a hemisphere, sphere, pyramid, cylinder, tetrahedron, parallelepiped, or polyhedron. Preferably, the gradient-modifying element is a pyramid, the most preferable pyramid a truncated right circular cone (a frustum). More preferred is a right circular cone with a vertex angle of between about 10° and about 135°, and even more preferred is a vertex angle of about 60° to about 120°. Preferably, the relationship among the dimension of the gradient-forming element extending from the source element to the release orifice (referred to herein as the height of the gradient-forming element) and the radii of the release orifice and the source element are such that the height of the gradient-forming element is less than about four times the ratio of the square of the radius of the source element to the radius of the release orifice. More preferably, the height of the gradient-forming element is less than about two times the aforementioned ratio, and most preferably, the height of the gradient-forming element is less than two times the aforesaid ratio but greater than one-tenth the aforementioned ratio.

In another preferred embodiment of the present invention, the foregoing device has a cylindrical gradient-forming element, one end of the cylinder in fluid registry with the source element, and the other end providing the release orifice. Preferably, the ratio of the radius of the hemisphere comprising the solute reservoir element to the radius of the source element is equal to or greater than about two, more preferably equal to or greater than five, and most preferably equal to or greater than ten. The height of the cylinder is preferably less than about four times its radius, more preferably less than about two times its radius, and most preferably 0.1 to 2 times its radius. Such devices are particularly useful for oral delivery of a therapeutic agent, although it is not so limiting.

In another embodiment, the device of the present invention may have a solute reservoir element in the shape of a truncated spherical cone or a truncated right circular cone. The gradient-forming element may have a shape among those described above; preferred is a cylindrical shape. Preferably, the radius of a hemisphere or portion thereof contained within the cone and representing the maximum internal diffusion surface is greater than twice the radius of the source element; more preferred is a hemisphere having a radius five to ten times the radius of the source element; most preferred is a hemisphere having a radius more than ten times the radius of the source element. The length of the gradient-forming element extending from the opening preferably is less than four times its radius, more preferably less than two times its radius, and most preferably, 0.1 to 2 times its radius. The gradient-forming element may also have a shape of a truncated right circular cone, wherein the base of the gradient-forming element is in fluid registry with the opening of the cone-shaped solute reservoir element, the dispenser thus having the appearance of a smaller cone extending from the vertex of the larger.

In yet another embodiment of the invention, modifications of dispenser with the foregoing characteristics but having the same or similar properties are embraced herein. For example, a dispenser particularly suitable for parenteral use, such as providing at a subcutaneous location, takes the form of a cylindrical-shaped solute reservoir element. A longitudinal sector of the cylinder is absent, the walls of the cylinder fluid- and solute-impervious. The absent longitudinal sector-shaped cavity in the cylinder forms the aforementioned gradient-forming element, and its interface exterior to the cylinder's overall shape forms the release orifice. The source element providing solute from the solute reservoir element to the gradient-forming element is provided in the form of a series of openings in at least one or both of the two flat faces forming the sector. A series of rows of openings parallel to the longitudinal axis of the cylinder are provided, with the rows more closely spaced to the interior of the sector (i.e., towards the center), and becoming less closely spaced approaching the exterior surface of the cylinder.

A similar configuration may also be provided by variously-shaped solute reservoir elements which are provided with a deep indentation, invagination or cavity contiguous with the exterior of the dispenser, the indentation forming the gradient-forming element. The solute reservoir element and the indentation are fluid- and solute-impervious. As in the previous embodiment, a series of openings between the solute reservoir element and the gradient-forming element provide the necessary source elements. If a series of rows of openings are provided, they may be more closely spaced distal to the interface between the gradient-forming element and the exterior of the dispenser, and become less-closely spaced towards the exterior. A solute reservoir element of the invention may have multiple cavity-type gradient-forming elements, of a combination of both cavity-type gradient-forming elements and the type of exterior gradient-forming element described above, such as a cone or cylindrical extension from the solute reservoir element. Thus, the invention embodies both interior and exterior gradient-forming elements, or combinations thereof in a single dispenser or device. Such devices provide the desired release characteristics as described herein, with a zero-order or near zero-order type kinetics and absence of an initial burst. As noted with the other dispensers, the geometry and dimensions of the devices with interior gradient-forming elements may be easily tailored to the particular application or needs of the device, including the location, duration, flux, permanence, biodegradability, among other factors.

Any discussion herein of the general features or aspects of the devices of the invention are applicable to any or all of the foregoing embodiments.

In one aspect the solute reservoir element of a device of the invention is empty. In another embodiment, the solute reservoir element contains a porous substrate. In yet another embodiment, the solute reservoir element contains one or more solutes, with or without a porous substrate. The release orifice may be coated with a material that is soluble under preselected conditions, such as a preselected pH.

The one or more solutes contained within a device of the invention may be, by way of non-limiting example, is a therapeutic agent. Examples of such therapeutic agents include a calcium salt, parathyroid hormone, antihypertensive agents, diuretics, sympatholytic drugs, vasodilators, calcium channel blockers, analgesics, opioids, non-steroidal anti-inflammatory agents, antihistamines, antidepressants, hypnotics, sedatives, antiepileptic agents, antiarrhythmic agents, antiparasitic agents, antimicrobial agents, chloroquine, anti-Parkinson agents, antineoplastic agents, contraceptives, hypoglycemics, electrolytes, vitamins, minerals, nutriceuticals, local anesthetics, diagnostic agents, peptide growth factors, hormones, cytokines, stimulants, amphetamine, methylphenidate, antianxiety agents, benzodiazepines, hematopoietic agents, erythropoietin, stem cell factor, interleukins, and mixtures thereof. In a preferred embodiment, the one or more solutes is an erythropoietin or a chloroquine.

The one or more solutes may be dissolved in a solvent or pharmaceutically acceptable vehicle, or it may be present in the device in a dry form. In one embodiment, the one or more solutes is not water soluble. A device of the invention may also include a solute-modifying agent.

In another broad aspect, the invention is directed to a method for delivering one or more solutes in a linear, sustained release fashion, by administering to a desired site of delivery at least one devices as mentioned above. Such delivery may be orally, sub-lingually, rectally, vaginally, sub-dermally, intramuscularly, ocularly, topically, nasally, aurically, intravenously, or directly into a particular anatomical location.

In a further broad aspect, the invention is directed to a kit comprising at least one device as mentioned above.

Variations in the design of the dispensers of the invention which provide the desired release properties are fully embraced herein. For example, a dispenser may have a single source element, a single gradient-forming element, and a single release orifice. Another variation comprises a plurality of release orifices. In another embodiment, a dispenser may have a plurality of source elements, each source element with its own gradient-forming element. In yet another embodiment, a gradient-forming element may be associated with several source elements, and in a further embodiment, a solute reservoir may have a plurality of such gradient-forming elements, each with multiple source elements. Moreover, a dispenser may have multiple gradient-forming elements, each of which provide a preselected but different release kinetics attributable to the entire dispenser.

The dispenser may have a shape selected from the group consisting of cone, cylinder, sphere, ellipse, hemisphere, capsule, rod, needle, and sheet. The dispenser or release orifice thereof may be covered or coated with a removable material to prevent release of the solute until the housing had resided in a particular location for a predetermined time period, or is subject to particular conditions which cause the material to become dislodged and initiate release.

The device of the invention may be adapted to hold one or more of the aforedescribed dispensers. By way of non-limiting examples, the device may be singly or multiply fenestrated to permit egress of solute to the environment after egress from the at least one dispenser contained therein, or the device may be designed to open or degrade to release the individual dispensers after a certain time period or under certain conditions. In a further example, the device may be provided with at least one exterior opening in fluid registry with a release orifice in a dispenser contained within. For a device with a plurality of such exterior openings, each orifice associated with a release orifice of a dispenser, each exterior opening is at least three release-orifice-radii apart from another, preferably ten radii apart.

The solute reservoir element may be filled with one or more solutes in adequate quantity to supply the source element of the device, and the gradient-forming element optionally may be filled with the one or more solutes.

In a second broad aspect, the present invention relates to a method for delivering one or more solutes in a linear, sustained release fashion, comprising administering to the site of delivery said solute or solutes in a device comprising at least one dispenser as described hereinabove, the dispenser containing at least one solute or capable of being filled with at least one solute. Using the device, the one or more solutes may be delivered into the body of an animal, for example, orally, sub-lingually, rectally, vaginally, sub-dermally, intramuscularly, ocularly, nasally, aurically, intravenously, on the surface of the skin, or directly into a specific anatomical location.

In a third aspect, the present invention relates to a kit, comprising a device for the continuous, linear, sustained release of a solute, the device comprising at least one dispenser as described hereinabove.

These and other aspects of the present invention will be better appreciated by reference to the following drawings and Detailed Description.

DETAILED DESCRIPTION OF THE INVENTION

Figure 1:
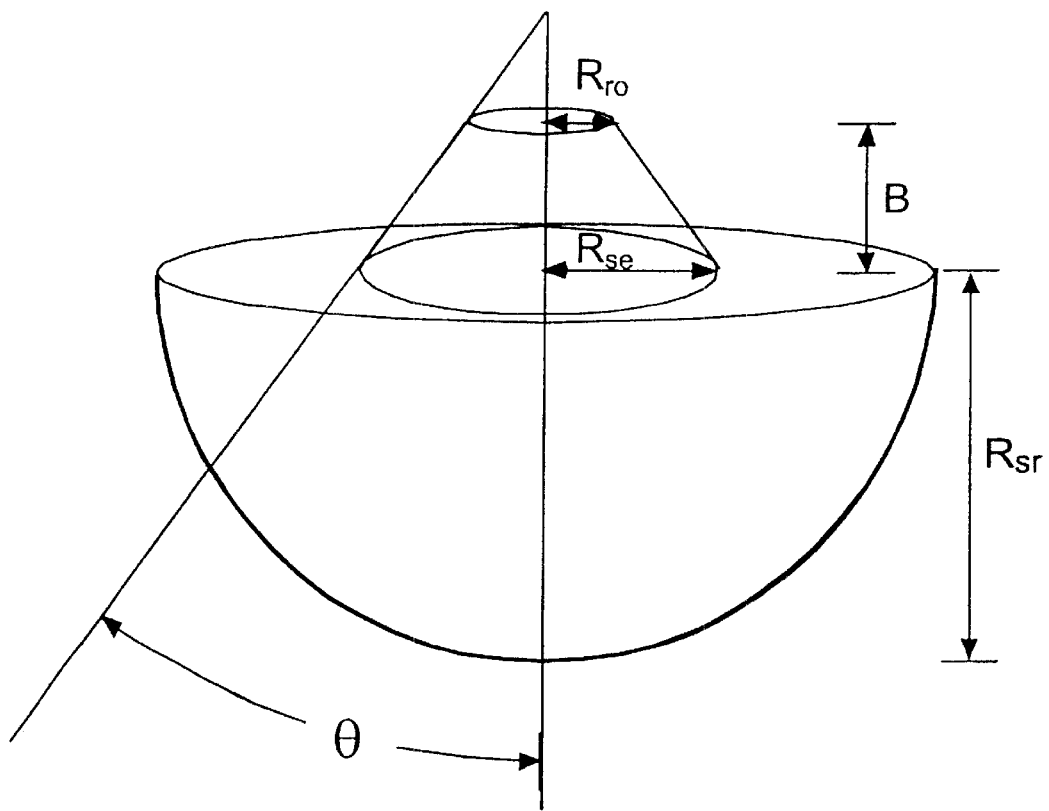
FIG. 1 depicts a schematic of the general shape of a non-limiting example of a dispenser of the invention, the example having a hemispherical solute reservoir element, a circular opening, the source element, in the center of the flat face of the hemisphere, and a frustoconical-shaped gradient-forming element having a release orifice from which solute is released.

The present invention is directed generally to various devices capable of delivering one or more solutes at a controlled, predetermined rate, over a prolonged period of time, with zero order or near zero order kinetics, without an initial burst. The parameters for a device with these desirable features may be determined by the teachings herein. The ability to control the delivery of a solute, by way of non-limiting example, a pharmacologically-active agent into the circulation of an animal at a controlled rate of release for an extended period without an initial burst, offers the advantages of maintaining therapeutically-effective levels over a prolonged period of time without waste of excess solute, for safe, effective, convenient and economical prophylaxis or therapy. Pharmaceutical agents with a narrow therapeutic index, for which an initial high level of release would be unacceptable, is but one example of a benefit of the instant devices over those previously known. Beyond pharmaceutical agents, the devices, methods and kits of the invention may be applied to the predetermined, controlled delivery of any solute or solutes from the instant devices into an exterior environment. The flexibility of the parameters of the present devices provides the ability to design a device with the aforementioned features for particular specifications which prolonged release and absence of initial burst are desired.

The invention herein is broadly drawn to a controlled release delivery device, and methods for delivering one or more solutes using the device, in which solute egresses from the device by diffusion from one or more openings in an otherwise fluid- and solute-impervious container. As will be seen below, the various elements which comprise the dispenser of the invention may be readily tailored to provide the particular desired release parameters such as duration and solute flux.

The dispenser of the present invention has at least four elements which contribute to its delivery properties. Each of the individual elements will be described in further detail below; the present discussion is directed to the interaction between the elements which provides the delivery features of the dispenser heretofore unachievable without the combination of these elements.

The solute reservoir element is provided to contain all or the bulk of the solute desirous of being delivered by the dispenser. At least one opening, termed the source element, is provided between the solute reservoir element and a chamber referred to as a gradient-forming element. The gradient-forming element has at least one release orifice. The gradient-forming element provides a means for creating a solute gradient extending from the source element towards the release orifice. This gradient is provided such that the desired solute release characteristics of the device are achieved. The gradient-forming element may or may not be filled with solute, so as to provide an initial bolus release ranging from a maximum level to no bolus release.

The solute reservoir element of a dispenser of the invention may be of any three-dimensional shape, such as but not limited to a hemisphere, sphere, pyramid, cylinder, tetrahedron, parallelepiped, or polyhedron. A hemisphere or a pyramid are preferred. Most preferred is a hemispherical-shaped solute reservoir element or a shape which efficiently comprises a hemisphere, i.e., a hemispherical shape resides within the overall shape of the solute reservoir element. As will be noted below, the dimensions of the solute reservoir element are described by the diameter of the largest hemisphere that can fit within the solute reservoir element with the position of the source element at the center of the diameter.

If the solute reservoir element is a hemisphere or a shape which comprises a hemisphere, the source element is preferably provided at the center of the flat face of the hemisphere or its equivalent. For example, a cube-shaped solute reservoir element with an opening (source element) at the center of one of the faces comprises a hemisphere having a radius equal to one-half the length of the sides.

As will be evident below, the preferred shapes to which the dispensers of the invention subscribe essentially have a hemisphere or a portion of a hemisphere at their core. Zero-order or near zero-order release occurs during the period of release when the enlarging cavity of egressed solute defines a hemispherical shape. Later release is linear, unlike other devices, which are by an exponential decay. Thus, a shape of the solute reservoir element which efficiently comprises a hemisphere will provide the least amount of wasted solute which may not be released by the desired kinetics, at the end of the working life of the device. However, for the reasons described herein, other reasons may dictate the shape of the device and the waste or lack of desired release profile may not be important for the particular use or location of the device. Thus, the efficient hemispherical shape of the solute reservoir element is preferred but not essential.

The release characteristics of the devices of the invention are provided for devices with certain preferred and most preferred characteristics, although the invention is not so limiting and one of skill in the art can readily design a device with the proper dimensions and solute content to provide the desired duration and release kinetics. In a preferred embodiment, the solute reservoir element is a hemisphere or comprises a hemisphere, and the source element is a circular opening centered on the flat face of the hemisphere, the source element having a radius. The gradient-forming element is a truncated right circular cone, also referred to as a frustum, whose base (the larger end) is in fluid registry with the source element, the base of the frustum and the opening forming the source element being one and the same and thus having the same radius. The truncated end of the cone (the vertex of the frustum) forms the release orifice. In the example of this embodiment, preferably, the ratio of the radius of the hemisphere, or portion thereof representing the maximum internal diffusion surface of the solute reservoir element, to the radius of the source element, is equal to or greater than about two, and more preferably, the ratio is equal to or greater than about five. Most preferably, the ratio is equal to or greater than about ten. As noted above, preferably the gradient-modifying element is a pyramid, the most preferable pyramid a truncated right circular cone. More preferred is a right circular cone with a vertex angle of between about 10° and about 135°, and even more preferred is a vertex angle of about 60° to about 120°. In this embodiment, preferably, the relationship among the linear dimension of the gradient-forming element extending from the source element to the release orifice (referred to herein as the height of the gradient-forming element), and the radii of the release orifice and the source element, are such that the height of the gradient-forming element is less than about four times the ratio of the square of the radius of the source element to the radius of the release orifice; more preferably, less than about two times the ratio, and most preferably, between about 2 times and about 0.1 times the ratio. Based on the dimensions labeled in FIG. 1, the foregoing relationships can be expressed mathematically as follows. With regard to the relationship between the radius of the hemisphere within the solute reservoir element, $R_{sr}$, and the radius of the source element $R_{se}$, preferably, $$\frac{R_{sr}}{R_{se}} \geq 2;$$

more preferably, $$\frac{R_{sr}}{R_{se}} \geq 5;$$

and most preferably, $$\frac{R_{sr}}{R_{se}} \geq 10.$$

With regard to the relationship between the height of the gradient-forming element, B, and the radius of the source element $R_{se}$ and the radius of the release orifice $R_{ro}$, preferably $$B \leq 4 \frac{R_{se}^2}{R_{ro}};$$

more preferably, $$B \leq 2 \frac{R_{se}^2}{R_{ro}};$$

and most preferably, $$\frac{R_{se}^2}{10 R_{ro}} \leq B \leq 2 \frac{R_{se}^2}{R_{ro}}.$$

B can be even less than 0.1 the foregoing.

The three-dimensional shapes of the solute reservoir element as well as other components of the devices or dispensers referred to herein may be described as follows. The term "pyramid" refers generally to a polyhedron with one face a polygon (the base) and all of the other faces triangles or polygons meeting at the vertex (the apex). The cross-section of a pyramid decreases from the base to vertex, and may decrease while maintaining the same cross-sectional shape, or the shape may change shape or orientation from base to tip, such as in a spiral cone. Various types of pyramids include cones, triangular pyramids, square pyramids, pentagonal pyramids, etc., depending on the number of sides. A cone is a particular type of pyramid in which the base and cross-section are circular. A truncated pyramid results in a shape called a frustum. A right circular cone has a flat base; a spherical cone has a spheroidal base. By way of illustration, a right circular cone with a vertex angle of about 30° has the shape of an empty ice cream cone, with the vertex being the "tip" and the base being the receiving portion for ice cream. The spherical cone as referred to herein may be described as particular three-dimensional cone-like geometric shape derived from a sphere, extending from the center of the sphere to the surface. A spherical cone has the shape of an ice-cream cone filled with only enough ice cream to provide a domed bulge above the rim of the cone, all points on the dome being equidistant from the tip of the cone. Generally, both the right circular cones and spherical cones may be referred to collectively herein as cones. To provide the openings, the cones may be truncated, i.e., the vertex ("tip") of the cone is cut off, preferably but not necessarily at a right angle to the longitudinal axis of the cone. The resulting shape is referred to as a frustoconical shape. As will be seen below, for the purposes of the invention, right circular cones and spherical cones may have vertex angles (i.e., the angle that forms the "point" of the cone) greater than zero and less than 180°. The shapes of the gradient-forming elements with small vertex angles may resemble needles; those with large vertex angles may approach the shape of a hemisphere. The value herein represented by θ (the Greek letter theta) is one-half of the vertex angle, as shown in FIG. 1.

In another preferred embodiment of the invention, a device similar to the example described above is provided, but having a cylindrical gradient-forming element. In this instance, the radius of the source element and that of the release orifice are the same. Preferably, the radius of the hemisphere or portion thereof representing the maximum internal diffusion surface is greater than twice the radius of the gradient-forming element (radius of the source element or the release orifice); more preferred is a hemisphere having a radius more than about five times the radius of the cylinder; and most preferred is a hemisphere having a radius more than ten times the radius of the cylinder. In addition, the height of the cylinder (gradient-forming element) extending from the source element to the opening preferably is less than four times the radius of the cylinder, more preferably less than two times the radius, and most preferably, 0.1 to 2 times the radius.

In another aspect of the invention, a device may comprise a single solute reservoir element with a plurality of source elements and associated gradient-forming elements each gradient-forming element having an orifice. Each source element and associated gradient-forming element is located maximally apart from the others such that the egressing solute about each source element slowly forms an ever-enlarging hemispherical cavity, each enlarging cavity maintaining separation from the others until one or more meet and fuse at some time after a prolonged period of zero-order release. For example, a capsule-shaped device may be prepared, comprising a single mass of solid solute, wherein each of one or more release orifices from which solute is released from the device is associated with a gradient-forming element and a source element extending from the single mass of solute. In a further embodiment, the release orifices may be covered or plugged with a material that is soluble in the small intestine but not in the stomach. Upon swallowing, the capsule passes through the stomach intact; on exposure to the small intestine, the coating dissolves, and release of solute is initiated, without initial burst and with near zero-order kinetics. Continued passage of the capsule through the digestive tract results in the desired delivery of the solute from the multiple openings over a prolonged period of time.

The term "device" and "dispenser" may be used interchangeably, although it is understood that a device of the invention may comprise one or more similar or dissimilar dispensers.

The terms "excipient" or "solute-modifying agent" is defined herein as any substance included in the solute reservoir element and/or gradient-modifying element of the device which is not the solute (e.g., therapeutic agent, perfume, algicide, etc.) and serves to alter the characteristics of the solute or of the operation of the device. Examples include compounds which alter the biological activity of the solute, for example to inactivate the biological activity of the solute during residence in the device, to aid in the precipitation of the solute within the device; to alter the pH to maintain stability; to promote solubility; to reduce or prevent immune recognition of the solute within the device; to dissuade entry of immune or other cells into the orifice; or to modulate the viscosity of the solute. Examples of such compounds are described hereinbelow. Excipients also extend to porous matrices, sponges, or other materials which are provided with the solute within the dispenser for the purpose of, for example, stabilizing the contents from agitation, spillage, etc.

A device of the invention comprises at least one of the above-described dispensers. It may be formed as a finished product in a shape to enhance the handling, mounting, delivery, fixation, swallowing, insertion, removal, and other esthetic and/or practical considerations in employing one or more dispensers for particular intended purposes, as will be elaborated upon further below. More than one dispenser may be contained within a housing; a plurality of similar or dissimilar dispensers, e.g., with different solutes or release characteristics, of different shapes, may be placed within a single housing.

In the devices of the present invention, the parts that determine the flux of solute include (1) a shaped cavity or housing wherein the one or more solutes is present (i.e., the solute reservoir element); (2) a fluid- and solute-impervious wall surrounding the cavity that is fenestrated with at least one opening (the source element); (3) a gradient-forming element into which the solute diffuses from the source element; and (4) a release orifice in the gradient-forming element from which solute flows out of the dispenser. The size of the solute reservoir element can range without limit, depending on the physical size of the device and can be very small to very large. In one embodiment, the dispensers consist of a cavity that is filled only with solute with or without binders or excipients. Acidic, basic, or amphoteric excipients may be included to promote solubility of the solute within the dispenser or maintaining solubility after release, such as is described in an example below. The structure of the device ensures that these modifying components persist with the other solute or solutes within the device to enable continuous solute delivery.

In another embodiment, the cavity of the solute reservoir element is filled with a porous or gel-like substrate that allows a stable concentration gradient to be established. The porous substrate can include, but is not limited to, agar, polyvinyl sponges, microporous beads, or polymer fibers. The nature of the porous substrate and the parameters of the gradient-forming element will predictably influence the rate of release of a solute from the device. Without being bound by any theory, the porous substrate effectively decreases the diffusion coefficient. Addition of a matrix may also provide a means for maintaining the concentration gradient inside the solute reservoir element in environments with extreme turbulence.

As mentioned above, the solute reservoir element has a geometrical shape that may be but is not necessarily symmetrical about the axis perpendicular to the plane of the source element. A symmetrical geometric shape for the dispensers of the invention is preferred as such shapes have been identified by calculation to allow for the most efficient prolonged nearly constant or linear delivery of solute. The impervious casing surrounding the dispenser or the entire device may be non-biodegradable or biodegradable. Alternately, the entire device or the release orifice(s) may be coated with a material that regulates release, e.g., a plug which dissolves under certain conditions and renders the orifice patent. Preferably, the device is made from one or more non-reactive and biocompatible polymers that include, but are not limited to, acrylonitrile polymers such as acrylonitrile-butadiene-styrene terpolymer; halogenated polymers or co-polymers such as polytetrafluoroethylene and polychlorotrifluoroethylene; polyimide; polysulfone; polycarbonate; polyethylene; polypropylene; polyvinylchloride-acrylic co-polymer; dialkyl fumarate; vinylidene chloride and polystyrene, methyl cellulose, polyethylene glycol or combinations thereof. Biodegradable polymers such as polylactides and polyesters, as well as modified cellulose derivatives such as methylcellulose, may be employed.

As mentioned above, prior art matrix or reservoir devices relying on diffusion for delivery have been unsatisfactory for a number of reasons including initial burst release, significant deviation from zero order or linear delivery, significant limitation of total dose delivered and rigid parameters, all of which make it difficult to adjust the delivery kinetics, including the duration of delivery. Prior art diffusion devices utilizing a small opening compared to the enclosed volume of solute are characterized by potentially quasi-zero order release for times late in the release after the initial burst or dumping of solute. Adjustment of release parameters is relatively insensitive to changing the dimensions of the opening, as flow of solute through the opening is directly proportional to its linear dimension.

An improvement of such devices can be obtained by utilizing devices of various sizes and shapes surrounded by a membrane impermeable to both the contents and the medium in which it is placed. This membrane is fenestrated at one location (defined by theoretical analysis as outlined elsewhere) by providing a source element (an opening), and is provided with a chamber in which the efflux of solute from the source element is modified by the gradient-forming element to provide the desired release characteristics at the release orifice. This chamber, referred to herein as a gradient-forming element, may be very much smaller in size than the solute reservoir element, and may appear only as a conical (or another shaped) bump on the solute reservoir element. The gradient-forming element initially may be devoid of solute, or it may be filled with solute, as the solute reservoir element, prior to release.

Prior art, fenestrated devices, whether containing a matrix or functioning as a reservoir only, operate in a well-described manner characterized by an "amplification" of the internal concentration gradient to provide a relatively high concentration at the surface of the fenestration. As diffusion of solute proceeds out of the device, diffusion fronts of constant concentration are established which take the form of concentric hemispheres for depths greater than one to two times the cross-sectional linear dimension of the fenestration. This means that there is increasing solute diffusion from the depths of the device to the surface, such as to tend to maintain the concentration at the opening at a steady state. If enough solute and the dimensions of these devices are optimized, nearly-linear release rates can be obtained for varying lengths of time. The initial release of solute from the fenestration occurs generally at a high concentration so that an initial burst of release occurs.

The present invention provides a method by which fenestrated devices of any configuration can be modified to provide a release closer to zero order, dampening of the initial burst of release, prolongation of delivery duration, and offer the ability to precisely and easily design a device of a required size or shape to deliver at a specific rate. In its most basic form, the gradient-forming element acts as a component to add impedance or resistance to the outflow of solute from the fenestration (source element). Upon initiation of diffusive release, which might occur, for example, when an orally-administered device is hydrated within the alimentary tract, the initially efflux of solute occurs into the empty gradient-forming element at a rate defined by the diffusive resistance of the gradient-forming element and the concentration of solute at the source element. Movement of solute from the interior of the device (solute reservoir element) is contributed by an increasing surface area of diffusion in direct relationship to distance from the entrance of the source element. In this manner, solute which leaves the interior of the device is replaced by solute from deeper within the device. As the diffusion front proceeds through the gradient-forming element, it reaches the external environment with a delay and initially at a much lower concentration than that of solute at the source element, i.e., at the fenestration or opening. After sufficient time, a steady-state rate of diffusion is established from the concentration gradient that has been established from the interior of the device through the gradient-forming element. This can be mathematically estimated using variations of the equation below.

The addition of a frustoconical-shaped gradient-forming element to a hemispheric solute reservoir element can increase and prolong the delivery rate compared to a hemisphere alone. This modification accomplishes this by maintaining the release orifice time-dependent concentration higher than it would be at an identical orifice in the face of the hemispherical solute reservoir element. The gradient-forming element prevents a too-rapid exit of solute from the device, which translates into a lower peak delivery rate, but at a higher and more prolonged quasi-steady state plateau.

The difference between the quasi-steady state release rates of a hemisphere compared to a frustoconical hemisphere can be seen by comparison of the relevant equations. The equation describing this quasi-steady state flux, i, from a hemisphere of radius $R_s$ with exit pore of radius $R_B$ is given by:

$$i = \frac{\pi R_B R_s D C_0}{\frac{(R_B - R_s)}{2} + \frac{\pi R_s}{4}}$$

in which the solute reservoir element contains a solute at an initial concentration $C_o$ and the solute has a diffusion coefficient D. The following equation describes quasi steady-state flux, i, from a dispenser with a frustoconical adjustable resistance element, such as is shown in FIG. 1. The solute reservoir element contains a solute at an initial concentration $C_o$, the radius of the solute reservoir element is $R_{sr}$, the source element has a radius $R_{se}$, the solute has a diffusion coefficient D, as indicated in FIG. 1, and the value of θ represents one-half of the vertex angle (i.e., the vertex angle is 2θ).

$$i = \frac{\pi R_{ro} R_{se} D C_0}{\frac{(R_{se} - R_{sr})R_{ro}}{R_{sr} 2} + \frac{\pi R_{se}}{4} + \frac{\tan\theta(R_{se} - R_{ro})}{2(1 - \cos\theta)}}$$

Figure 2:
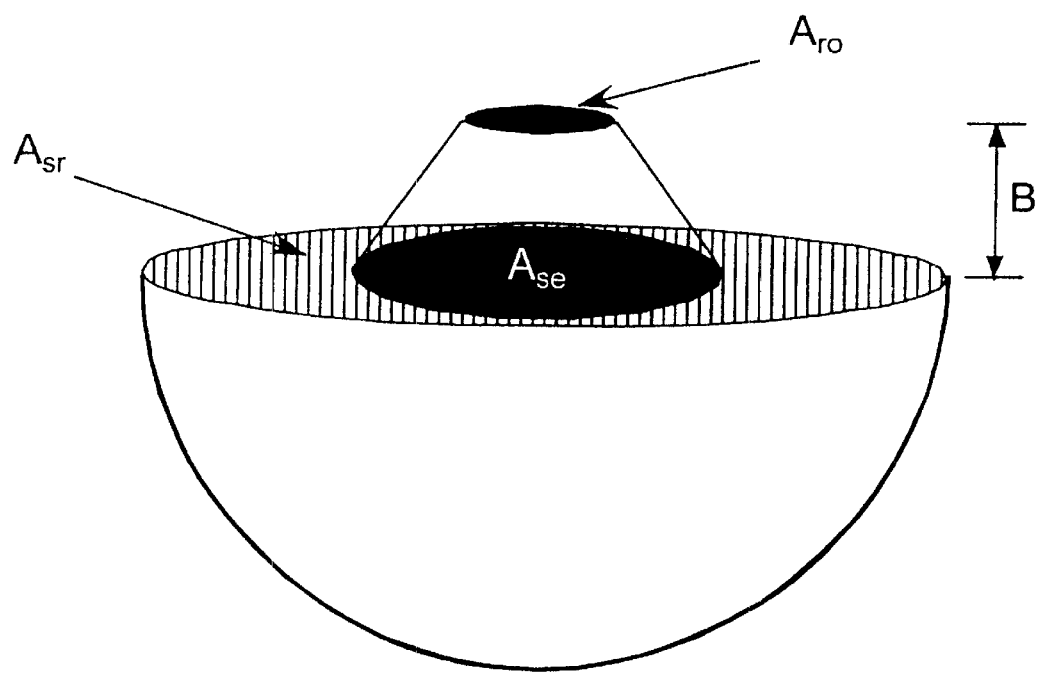
FIG. 2 shows another schematic of the device of FIG. 1, with certain surfaces labeled.

The preferred dimensions of the device are described by expressing the cross-sectional area in terms of corresponding circles with equivalent surface areas. As shown in FIG. 2, the source element has cross-sectional area $A_{se}$, and the release orifice has a cross-sectional area represented by $A_{ro}$. Release characteristics for devices in which the source element and/or release orifice are not circular can be calculated by determining the equivalent radius of the opening were it to have an equal circular cross-sectional area. Alternate openings may be, by way of non-limiting example, elliptical and square, and the shape of the gradient-forming element correspondingly shaped.

In the instance wherein the gradient-forming element is a cylinder, such as is shown in FIG. 15, and thus $R_{ro}$ and $R_{se}$ are the same, the height of the cylinder being B, the steady-state release is described by the following formula:

$$i = \frac{\pi R_{se}^2 D C_0}{\frac{(R_{se} - R_{sr}) R_{se}}{2 R_{sr}} + \frac{\pi R_{se}}{4} + B}.$$

Such a device with a cylindrical device may be easier to manufacture, as, for example, the finished dispenser can have the shape of a hemisphere with the source element and gradient-forming element at the center of the flat face, in which the thickness of the coating on the flat surface provides the height of the gradient-forming element.

In the instance wherein the gradient-forming element is cylindrical, and the solute reservoir element may be hemispherical or comprises a hemispherical shape with the source element centered on the flat face of the hemisphere, preferably, the radius of the hemisphere or portion thereof representing the maximum internal diffusion surface is equal to or greater than greater than about twice the radius of the gradient-forming element (radius of the source element or the release orifice); more preferred is a hemisphere having a radius more than about five times the radius of the cylinder; and most preferred is a hemisphere having a radius equal to or more than ten times the radius of the cylinder. In addition, the height of the cylinder (gradient-forming element) extending from the source element to the opening preferably is less than four times the radius of the cylinder, more preferably less than two times the radius, and most preferably, 0.1 to 2 times the radius. The ratio of the radius of the cylinder to the radius of the hemisphere which gives the maximum efflux while still blunting the initial surge of release is 0.08 to 0.086, or about 1:12. These parameters are non-limiting and merely illustrative.

In another preferred embodiment, the solute reservoir element of the dispenser of the invention has the shape of a truncated right circular cone or a truncated spherical cone. These shapes are described above. The gradient-forming element may have any shape which provides the desired release characteristics, such as but not limited to either a frustoconical or cylindrical shape. These preferred shapes of the gradient-forming element are as described hereinabove with regard to the hemispherical-shaped solute reservoir element. All other aspects and additional features of the foregoing dispensers are applicable to this embodiment as well.

In this particular embodiment, the more preferred cone-shaped solute reservoir element has a vertex angle of between about 10° and about 135°, and even more preferred is a cone with a vertex angle of about 60° to about 120°. The cone with a vertex angle of 180° is a hemisphere, and is described previously. The source element is preferably provided at the vertex of the solute reservoir element, i.e., where the tip of the cone is truncated. For a device as described with a conical-shaped solute reservoir element and a frustoconical or cylindrical gradient-forming element, the foregoing equations may be used to indicate the solute flux from the release orifice of the device, when the radius of the largest hemispherical solute reservoir contained within the cone, and the source element positioned at the vertex of the cone, is used. In addition, the preferred and most preferred embodiments are similar. By way of non-limiting example, the useful range of device parameters of the above-mentioned device with a cylindrical gradient-forming element of the invention are as follows. Rsphere (the maximum radius of the internal diffusion surfaces) is preferably greater than twice the radius of the gradient-forming element, more preferably 5 to 10 times the radius, and most preferably greater than 10 times the radius. The ratio of the radius of the gradient-forming element to the radius of the sphere which gives the maximum efflux while still blunting the initial surge of release is 0.080 to 0.086, or about 1:12. With regard to the height and radius of the gradient-forming element, the gradient-forming element length preferably may be less than 4 times its radius, more preferably less than 2 times its radius, and most preferably 0.1 to 2 times its radius. These parameters are non-limiting and merely illustrative.

Thus, by following the teachings herein and the foregoing equations, the skilled artisan may readily construct a device for a particular application, thus delivering a particular solute or solutes over an extended period of time with zero order or near zero order kinetics. Any reduced delivery rate that is dictated to provide the desired release characteristics for a particular size or shape of device may be offset by increasing the concentration of the solute ($C_0$) within the solute reservoir element, or by changing the geometry by the teachings conveyed herein.

In one embodiment, the release orifice of the device is coated (and/or the gradient-forming element filled) with a material that is soluble only under a particular set of conditions. In a preferred embodiment, the release orifice of a device used for oral delivery of solutes to the body of an animal are coated with a material that is soluble only at a basic pH, thus enabling the solute to be released in the intestines of the animal rather than in the stomach.

Orifices or openings can be generated by methods well known to those skilled in the art. For example, openings can be formed by, inter alia, etched nuclear tracking; a laser, sonic or mechanical drilling; or electrical discharge; etching; or by molding. The devices may be prepared by any method which provides the dispenser(s) and its housing, such as microfabrication, injection molding, etching from a solid block in the shape of the housing, etc. The size of the device is governed by the release characteristics, the total amount of solute(s) to be delivered, and may range from microscopic devices, for example, to enter the vascular circulation of animals, to very large devices, such as may be placed in a water treatment tank, swimming pool or reservoir, for sustained release of algicide, etc.

In one embodiment, the device has one dispenser and one release orifice. In another embodiment, the device has more than one dispenser, each separated by impervious material and for which the release orifices are placed far enough apart so as to not interfere with each other. In one embodiment, the one or more dispensers contain one or more solute materials. In another embodiment, a device with more than one dispenser, each separated by impervious material, has one release orifice for each dispenser housing.

In some cases, a hemispherical, conical, cubic or other shaped dispenser designed in accordance with the foregoing teaching may not be suitable for the finished device, and it will be desirous to surround or provide the dispenser with an alternate finished shape. Such considerations may be done, for example, to enhance consumer acceptance of the device, or to eliminate edges or protruding parts to ease swallowing or insertion and, if necessary, retrieval, from a body cavity. Such shapes may include, but are not limited to, a cone, cylinder, sphere, ellipse, hemisphere, capsule, rod, needle, or sheet. The foregoing non-limiting list is the shape of the finished device. In some instances, the dispenser of the device and the housing may be one continuous material, wherein, for example, an inner hemispherical-shaped solute reservoir element and associated gradient-forming element are built up of, or hollowed out from, the same impervious material to form a finished housing of a different and more user-friendly shape. The orifice(s) of the dispenser(s) may be fabricated to open to the surface of the housing to provide the exit from the device directly into the compartment in which the device is placed; alternatively, the dispenser(s) may release into the interior of the housing and the released solute pass into the exterior compartment through one or more outlets. The housing may have numerous outlets, such as a porous or regularly perforated material, from which the solute is rapidly moved into the exterior compartment. The device may be provided such that before use, it may be opened for placing within the dispenser, the solute, which may be for example in the form of a pre-manufactured prescription drug tablet with no provision for controlled release kinetics. These and other details of the particular features of the devices are embraced within the teachings herein, and one of skill in the art will readily design an outer casing or housing to house the one or more dispensers to provide a compatible product to meet the needs of the particular application.

For example, an elliptical or capsule-shaped housing may be provided to aid in the swallowing of a device that will release solute during transit through the digestive tract. The gradient-forming element(s) of the dispenser(s) may empty to the exterior from outlets flush to the surface of the housing. A smooth-sided device without edges is particularly desirable for other in-vivo uses as mentioned above, particularly for introduction into any body cavity or orifice, or for surgical implantation and, if necessary, later retrieval. In another embodiment, an air freshener for using in a moving vehicle which releases from a volatile liquid at a constant rate is provided in the shape of a ornamental canister which can be affixed to the dashboard or hung from the rear-view mirror. The solute, in this case a liquid, is kept from agitation by the solute reservoir element housing being filled with sponges or microporous beads in which the fragrant liquid is saturated. The finished shapes of the housings of such devices may integrate into the particular location of use, or incorporate esthetic or other design features for acceptability of the end user.

Those of skill in the art will recognize in the design for a device with more than one dispenser, that not all of the dispensers necessarily need to have the same release parameters or shape. A device may have a dispenser with one particular shaped and sized gradient-forming element, and another with another set of parameters, for example, a device comprising a form of chlorine for disinfecting a swimming pool may have one dispenser with no gradient-forming element, the dispenser containing the amount of chlorine necessary to "shock" the pool, for example, after a period of non-use or first use of the season. The shock provides a large amount of chlorine that would be undesirable for human enjoyment. After the initial burst, the chlorine dissipates after a few days. A second dispenser in the device comprises a gradient-forming element to provide zero-order release of chlorine of an amount compatible with swimming but to maintain antisepsis, for an extended period such as one month. Thus, the dispenser of the present invention may be combined with other devices to achieve desirable features for the intended purposes of controlled release.

Devices of the present invention can be made in any size, including but not limited to devices on the order of a millimeter or less that can be put into a capsule and swallowed to those that are on the order of tens of centimeters or larger, depending on the intended use.

In one embodiment, many devices, each carrying an amount of solute, are placed inside a capsule to be swallowed, such that, when the capsule breaks open or the coating dissolves, the devices are released into the body of the animal and solute is delivered from each device. Devices of the invention can be made from any material. In another embodiment, the devices are biodegradable. In yet another embodiment, the devices are made from non-biodegradable material.

A desired duration of release may be provided by configuring the device as described herein. In one embodiment, the methods of the invention can be used to deliver solutes in a linear fashion over a time period of from about 1 hour to about 1 month, more preferably for a duration of from about 5 hours to about 2 weeks, most preferably for a duration of from about 12 hours to about 48 hours. In a particularly preferred embodiment, the methods of the invention are used to deliver solutes in a linear fashion to the body of an animal over a time period of from about 8 hours to about 24 hours.

One or more solute can be delivered using the devices of the present invention. In one embodiment, the one or more solutes delivered by the devices of the present invention are beneficial agents, such as therapeutic or prophylactic agents, that are delivered to the body of an animal. These beneficial agents include, but are not limited to, antihypertensive agents such as diuretics, sympatholytic drags, vasodilators and calcium channel blockers, analgesics such as opioids and non-steroidal anti-inflammatory agents, antihistamines, antidepressants, hypnotics, sedatives, antiepileptic agents, antiarrhythmic agents, antiparasitic agents, antimicrobial agents, anti-Parkinson agents, antineoplastic agents, contraceptives, hypoglycemics, electrolytes, vitamins, minerals, nutriceuticals, local anesthetics, diagnostic agents, peptide growth factors, hormones and cytokines, stimulants such as amphetamine and methylphenidate, antianxiety agents such as benzodiazepines, and hematopoietic agents such as erythropoietin, stem cell factor, interleukins, and mixtures thereof. Such agents may also be diagnostic agents, such as radioimaging agents or substances for evaluating metabolism or clearance, e.g., hepatic or renal function. In a preferred embodiment, the beneficial agent is erythropoietin. In another preferred embodiment, the beneficial agent is chloroquine, glipizide, calcium salts or parathyroid hormone. In one embodiment, a single beneficial agent is administered using the devices of the invention. In another embodiment, combinations of two or more beneficial agents are administered using the devices of the invention. For example, a decongestant and an antihistamine can be co-delivered to the body of an animal for treatment of cold symptoms using the devices of the invention. As noted above, a single device of the invention may comprise a plurality of release units, each of which may house a different solute and release it with particular desirable kinetics, such that the co-delivery of solutes may be optimized for each individual solute. Alternatively, one dispenser may comprise a plurality of solutes which are co-dispensed with the same kinetics.

In one embodiment, the one (or more) solute is dissolved in a solvent. Those skilled in the art will appreciate that the type of solvent used to dissolve the one or more solutes depends on the solubility properties of the one or more solutes. The solvent may be an aqueous solvent, an oil or non-aqueous medium. In one embodiment, the one or more solutes is a beneficial agent to be administered to the body of an animal and can be administered alone or together with a pharmaceutically acceptable vehicle. In a specific embodiment, the term "pharmaceutically acceptable" means approved by a regulatory agency of the federal or a state government or listed in the U.S. Pharmacopeia or other generally recognized pharmacopeia for use in mammals. The term "vehicle" refers to a diluent, adjuvant, excipient, or carrier with which the one or more solutes is administered. Such pharmaceutical vehicles are preferably liquids, such as water and oils, including those of petroleum, animal, vegetable or synthetic origin, such as peanut oil, soybean oil, mineral oil, sesame oil and the like. When administered to a mammal, the one or more solutes and pharmaceutically acceptable vehicles are preferably sterile. Saline solutions and aqueous dextrose and glycerol solutions can also be employed as liquid vehicles. The one or more solutes, if desired, can also be administered with required amounts of wetting or emulsifying agents, or pH buffering agents.

Such agents in the device other than the agent desired to be delivered are generally referred to herein as solute-modifying agents. Further to the above, other excipients may be used to modify the one or more solutes or the properties of the device, such as but not limited to the following activities. Agents to reduce the immunodetection of the solute(s) in the device or to prevent colonization and clogging by mobile cells of the animal or environment in which it is implanted or placed, such as white blood cells or fouling bacteria or other microorganisms; agents to chelate calcium to prevent clotting of plasma or blood within the device; polymers to increase the viscosity of the solute within the primary dispenser housing of the device; surfactants to maintain solubility; etc. Such agents may or may not be released from the device along with the desired solute(s); upon release, such agents may dissociate from the solute(s) or be diluted such that they have no or minimal effect on the goal of the device and the methods for delivery of solute.

In another embodiment, the one or more solutes to be delivered using the devices of the invention are not dissolved in a solvent, but are present in the device in dry form. In this embodiment, the one or more solutes are dissolved or suspended in fluid when the device is immersed, e.g., in the gastrointestinal fluids of an animal if the device is swallowed, or in water if the device is used to deliver algicides to a swimming pool. The one or more solutes can be present in the device as, inter alia, a powder, a crystal, an amorphous solid, and the like.

In another embodiment, a user-fillable or refillable device may be prepared with the features described hereinabove, such that, for example, a prepared dosage form of a pharmaceutical agent, such as a chloroquine tablet, may be loaded into a device by the user, swallowed, and prolonged linear delivery of the pharmaceutical agent achieved in the body. An implanted device could be refilled at intervals, for example, by transcutaneous injection into the device. Such devices may be biodegradable. Another such device to release perfume at zero-order may be filled by the user and then carried on the person, for example, in the form of jewelry or secreted in the clothing, to provide a pleasant, continuous level of local fragrance.

The present invention also includes methods for delivering solutes in a linear fashion using the devices of the invention. In a preferred embodiment, the methods of the invention are used to deliver one or more solutes to the body of an animal. In one embodiment, the methods of the invention are used to deliver one or more solutes that are poorly soluble in aqueous media to the body of an animal. In this embodiment, the one or more solutes in the device are dissolved in an oil or other non-aqueous medium. Without being bound by any theory, the applicants observe that the rate of diffusion of a non-water-soluble solute from a device of the invention is partly dependent on the partition coefficient of the solute in water. In another embodiment, the one or more solutes in the device are in dry form, and are dissolved or suspended in liquid only when the device is immersed. The methods of the present invention can be used to deliver substances to the body of an animal by various routes including, but not limited to, orally, sub-lingually, rectally, vaginally, sub-dermally, topically, intramuscularly, ocularly, nasally, aurically, intraperitoneally and intravenously. In one embodiment, the methods of the present invention employ an injectable device of the invention made from biodegradable material. In another embodiment, the device could be incorporated into a dermal patch to deliver agents transdermally.

The devices of the invention may deliver other solutes, including but not limited to fragrances, deodorizers and other airborne volatiles such as contained in air fresheners; industrial chemicals, such as may be delivered at a sustained rate to an industrial process; disinfectants such as chlorine or bromine for delivery into swimming pools and hot tubs; delivery of mosquito larvicide to ponds; delivery of fertilizer to plants. A device of the invention may be placed in a conduit or stream through which a fluid passes, the device delivering solute into the moving stream. These examples are merely illustrative and non-limiting with regard to the wide variety of uses to which the instant devices and method may be put.

The present invention further includes kits for the delivery of one or more solutes. Kits of the invention comprise one or more devices of the invention. Kits of the invention can be used to deliver one or more solutes to the body of an animal, to water tanks, swimming pools, hot tubs, plants, toilets, septic tanks, textiles, water towers, aquaria, ponds, and for industrial manufacturing processes. The devices of the invention may be provided in reuseable form, such as a device which may be opened for refilling. The device of the kit may be provided in an empty form without any solute, for filling by the user before placement into the intended environment.

Manufacturing processes can be straighforwardly accomplished using methods well-known to one knowledgeable in the art of pharmaceutics.

Figure 10:
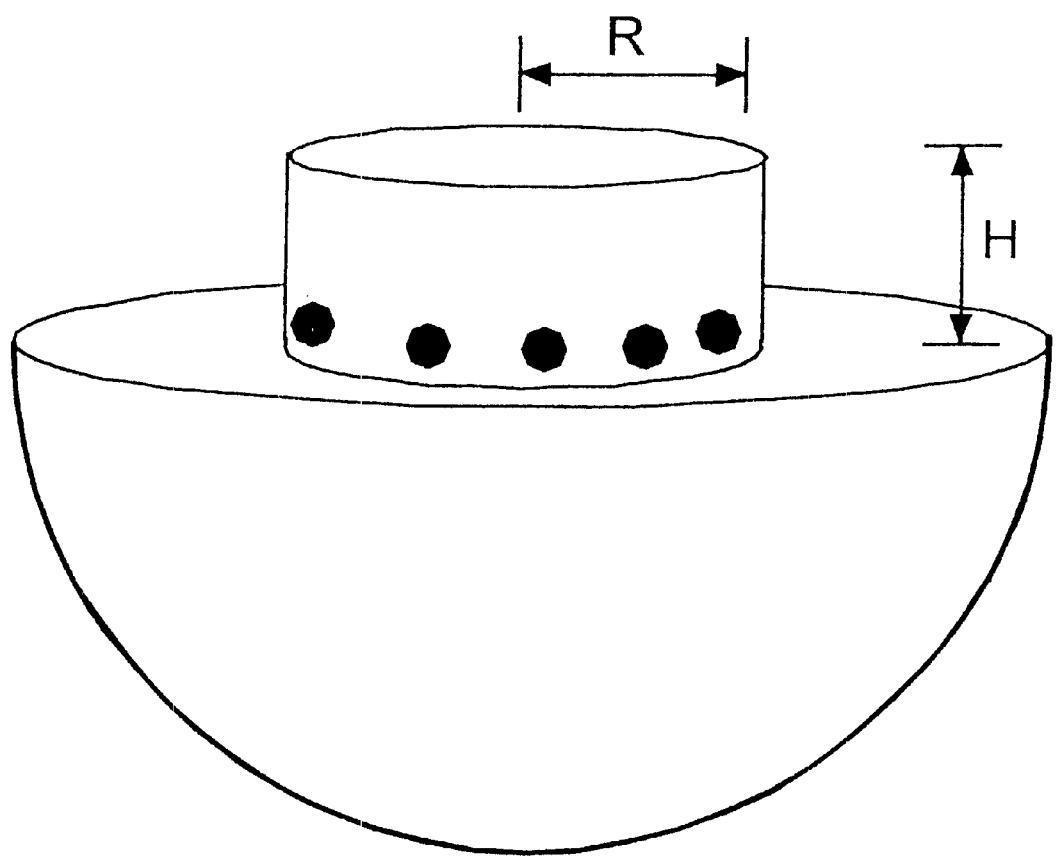
FIG. 10 shows a device of the invention with a hemispherical solute reservoir element, a tubular gradient-forming element, with a plurality of release orifices provided around the base of the gradient-forming element.
Figure 11:
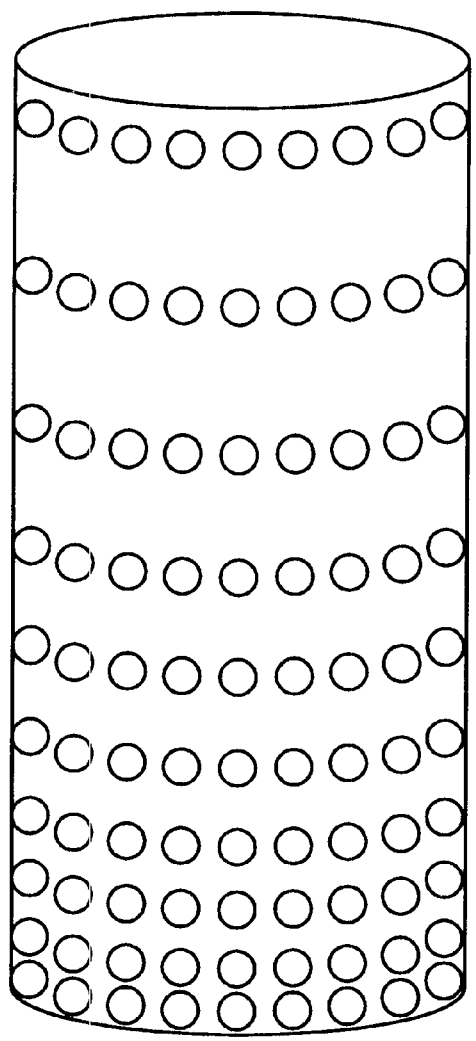
FIG. 11 shows a device of the invention having a cube-shaped solute reservoir element, with the gradient-forming element provided as a tubular cavity extending partway through the solute reservoir element. Source elements are provided as a series of circumferential fenestrations about the tubular cavity, closely spaced near the interior-most part of the gradient-forming element and becoming more distantly spaced approaching the single release orifice at the surface of the cube.
Figure 12:
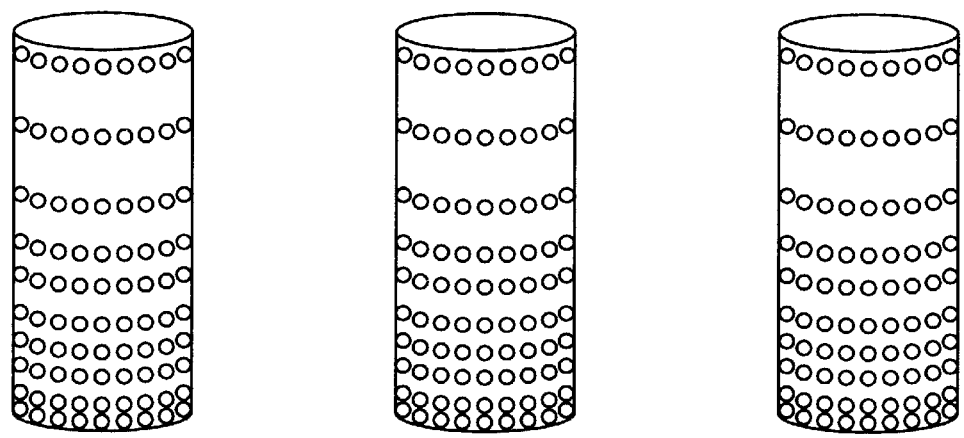
FIG. 12 depicts a device similar to that in FIG. 11, with three gradient-forming elements in a single solute reservoir element.
Figure 13:
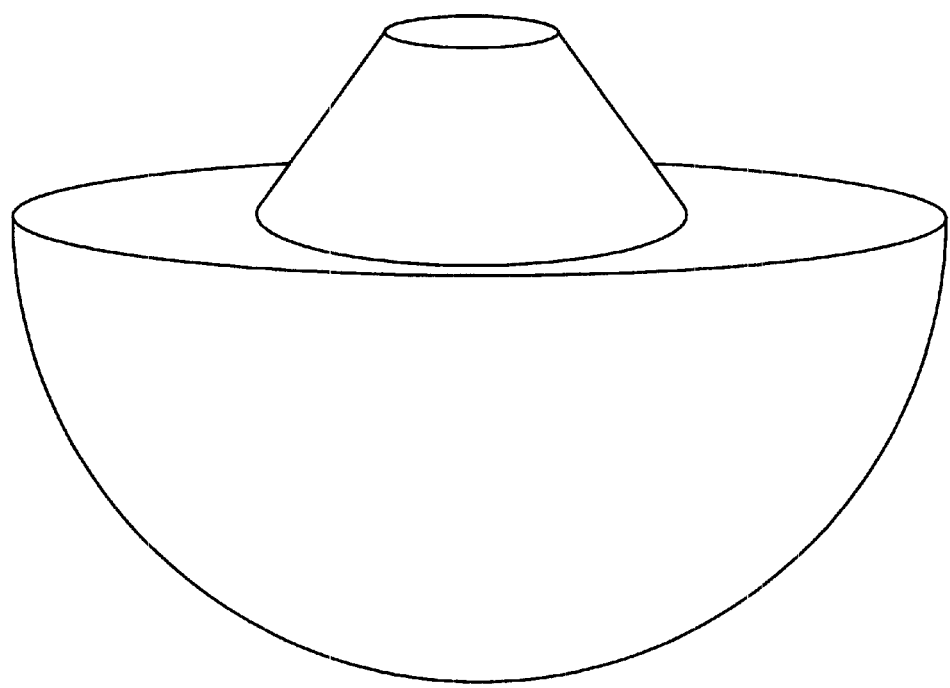
FIG. 13 shows a three-dimensional rendition of a preferred device of the invention which comprises a single source element and single gradient-forming element.

In a further embodiment of the invention, devices with dispensers illustrated in FIGS. 10–12 are provided. In the example of FIG. 10, a plurality of release orifices are provided around the base of a tubular gradient-forming element. In FIGS. 11–13, a plurality of source elements are provided to a gradient-forming element which is provided in the form of a tubular indentation into the solute reservoir element, the source elements provided in circumferential bands in the gradient-forming element, with increasing inter-band distance as the bands approach the release orifice, which is flush with the surface of the solute reservoir element. Both of these devices provide, in accordance with the present invention, the source elements and gradient-modifying elements to provide desirable release characteristics as described herein.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

A hemispherical brass mold was filled with chloroquine powder (approximately 500 mg) and was then compressed using a hydraulic press (6 ton) for 1 minute using either a flat or concave frustoconical piston to obtain tablets with the following dimensions:

| piston: | flat | frustoconical |
| --- | --- | --- |
| $R_{sr}$ | 0.635 cm | 0.635 cm |
| $R_{se}$ | 0.15 cm | 0.15 cm |
| $R_{ro}$ | 0.15 cm | 0.075 cm |
| θ | 0° | 45° |
| B | 0.25 cm | 0.25 cm |
| $C_0$ | 900 mg/mL | 900 mg/mL |

Figure 3:
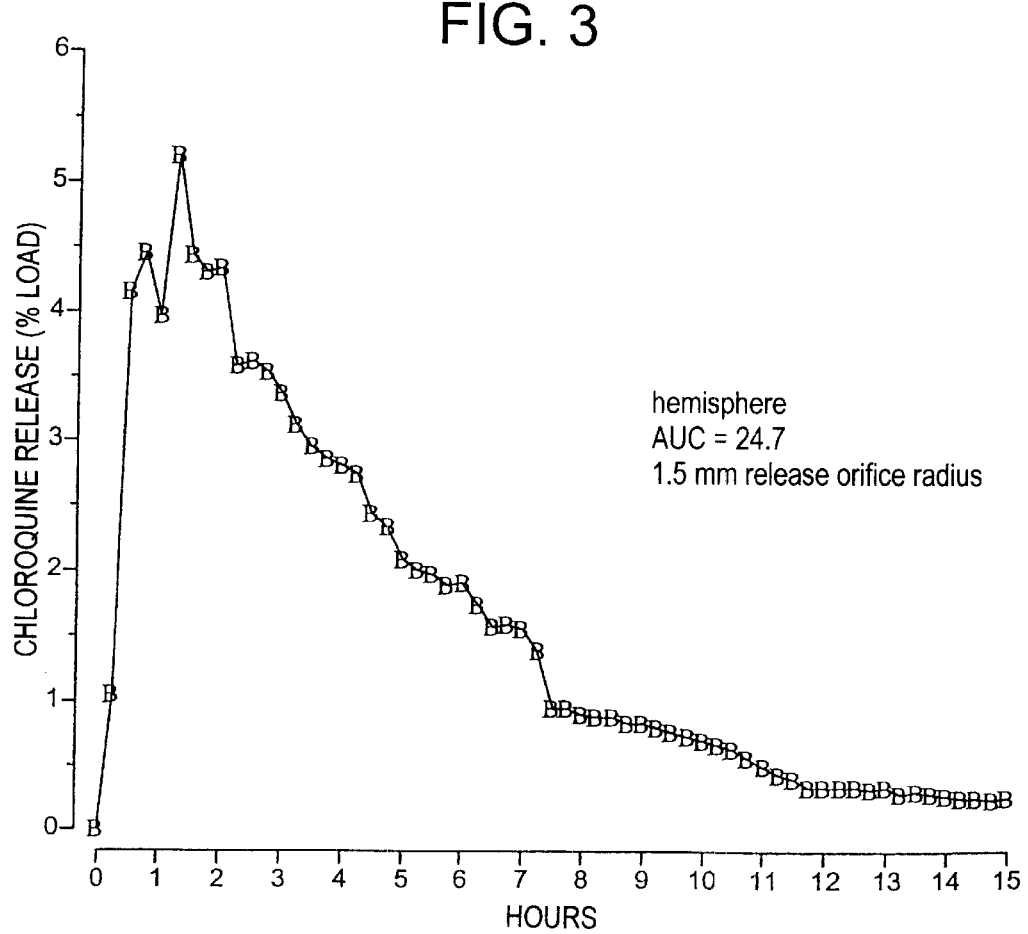
FIG. 3 depicts the time-dependent efflux of chloroquine from a prior art, hemispherical-shaped device with a 1.5 mm fenestration.
Figure 4:
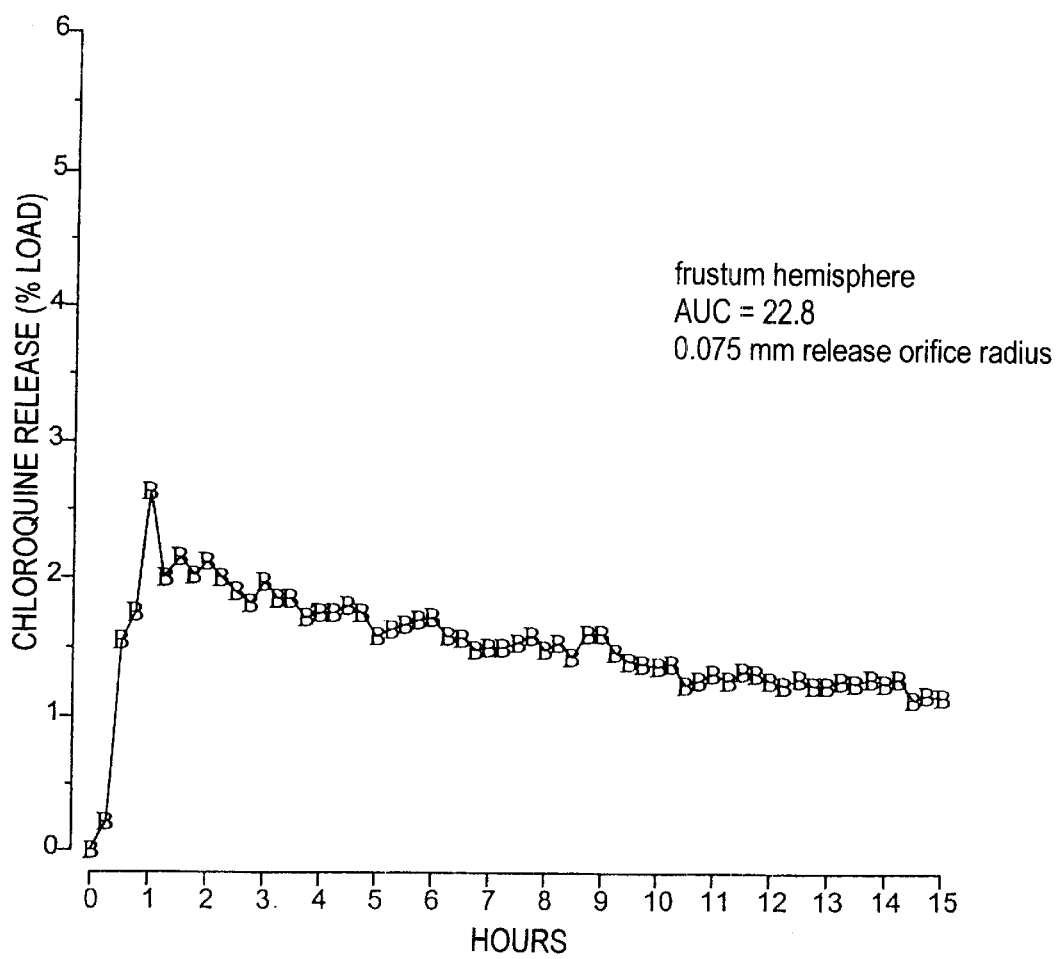
FIG. 4 shows the time-dependent efflux of chloroquine from a hemispherical solute reservoir element with a 1.5 mm radius fenestration and a frustoconical gradient-forming element with a 0.75 mm radius release orifice.

The time dependent efflux of chloroquine was determined using the ascending-column method (Langenbucher, 1969;

*J. Pharm. Sci.* 59: 1265). The release rates of these two devices (as percent chloroquine load) is shown in FIGS. 3 and 4. Here, the hemisphere and frustoconical hemisphere have similar total release (area under the curve; AUC) but that with the frustoconical release modulator (FIG. 4), the peak release is about 50% of the hemisphere alone, but is maintained for a prolonged period of time.

Figure 5:
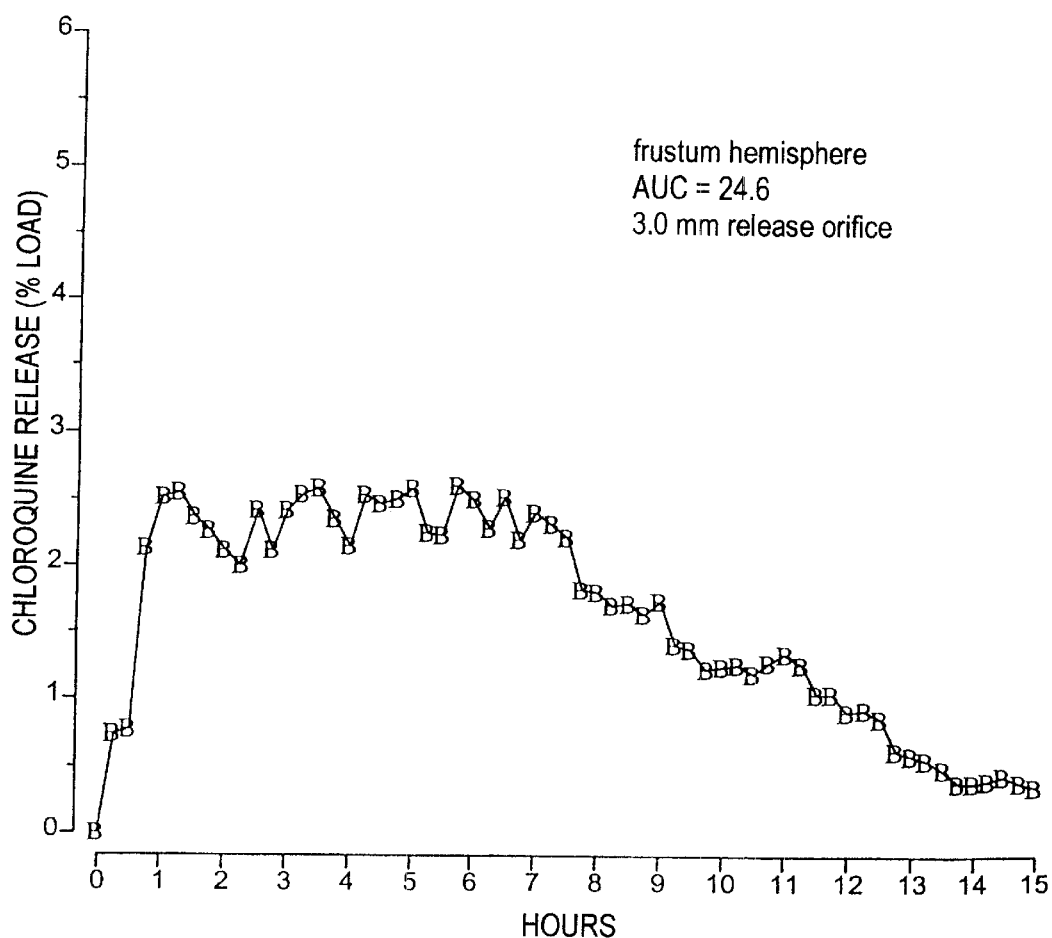
FIG. 5 shows the time-dependent efflux of chloroquine from a hemispherical solute reservoir element with a frustoconical gradient-forming element with a 3.0 mm release orifice.

The release kinetics of the frustoconical device can be changed in a number of ways by specifying different parameters, as will be evident to one skilled in the art. For example, by doubling the size of the exit orifice, from a radius of 0.075 cm to 0.150 cm, a higher, sustained peak release is obtained (FIG. 5), but at the expense of a shorter delivery duration.

EXAMPLE 2

Figure 6:
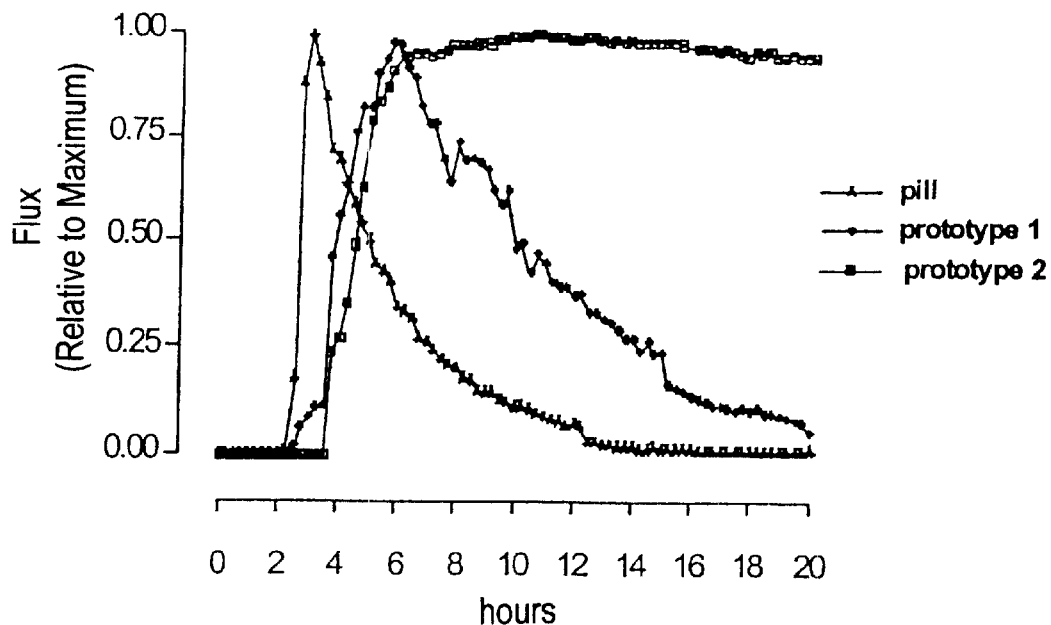
FIG. 6 compares the release from a marketed chloroquine preparation (ARALEN) to two devices of the present invention.

Comparison was made between the release kinetics of chloroquine using a device of the present invention and an immediate release preparation, ARALEN. Crystalline chloroquine was placed in two devices, designed to either deliver or not deliver a loading dose of drug. The filled devices were placed in a chamber through which water was pumped at a rate of 0.75 ml/min. Perfusate was continuously collected at 15-minute intervals by a fraction collector. The chloroquine content of the fractions was determined by light absorption with reference to a standard curve. The closed triangles define the release rate of the device delivering a loading dose, while the open circles define the release rate of the device with a blunted loading dose (FIG. 6). Both devices reached a steady-state release of approximately 250 microgram/15 minutes. The results demonstrate the ability of the devices as described herein to release chloroquine in a controlled manner. Compared to the marketed preparation's exponential decrease of the release rate over time, device 1 exhibits a linear decline of the release rate and device 2 approximates a zero order release rate.

Figure 7:
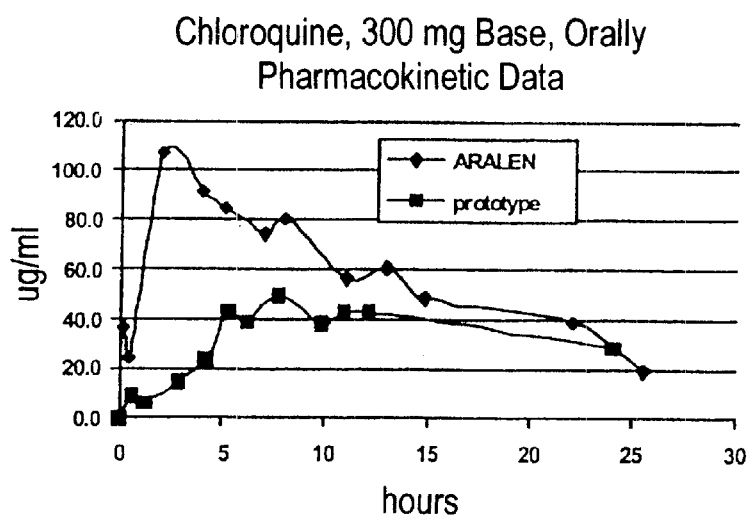
FIG. 7 compares in-vivo release of chloroquine from a prior art device to one of the present invention.

FIG. 7 shows the pharmacokinetic behavior in a human male subject of the commercially-available chloroquine formulation ARALEN and a prototype device of the present invention, both preparations containing 300 mg of base chloroquine. The data are consistent with the release dynamics of the two preparations (see FIG. 6). The device of the present intention achieved serum levels within a narrow range over a 24 hour period, when compared to ARALEN.

Figure 8:
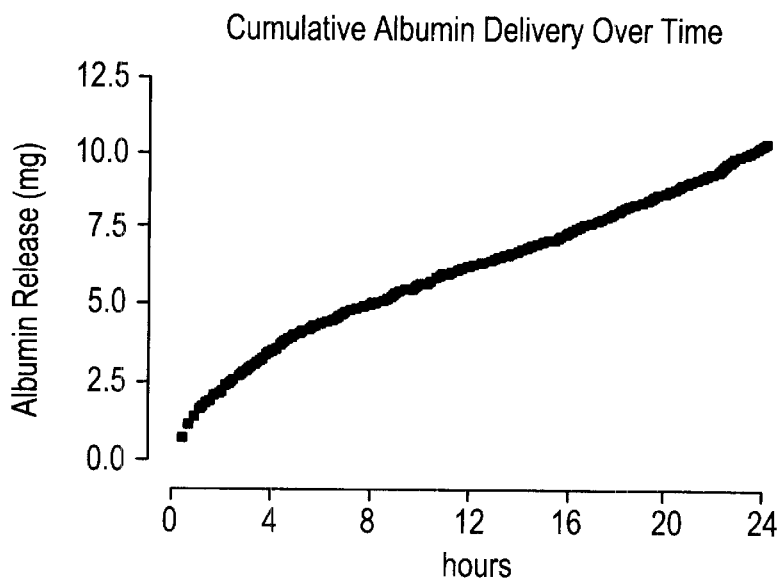
FIG. 8 depicts the cumulative release of albumin from a device of the invention over 24 hours.

FIG. 8 shows data for the cumulative release of the macromolecule albumin from a controlled-release device of the present invention. The data reflect zero order rate release of albumin over a duration of 24 hours. Bovine serum albumin (MW 68,000) was dissolved in phosphate buffered saline and loaded into a device designed to deliver a loading dose. After an initial burst release, the rate becomes constant. Data are plotted as the cumulated delivery of albumin over time, measured as described for FIG. 5. Approximately 10 mg was delivered in 24 hours.

Figure 9:
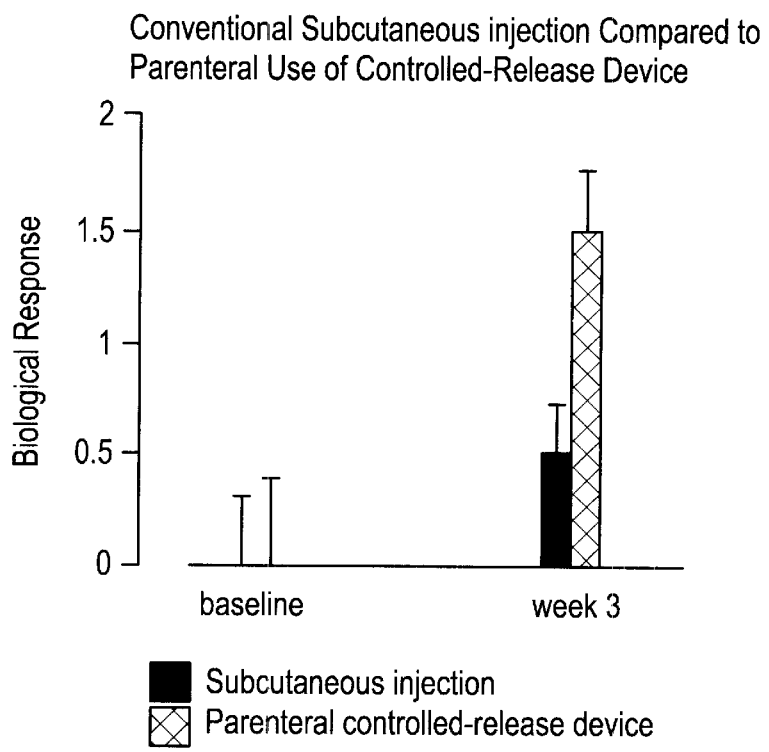
FIG. 9 shows the results of an in-vivo experiment comparing the response to a single dose of subcutaneously-administered erythropoietin to a parenterally-implanted device of the invention containing the same agent, which was delivered over a three-week period.

FIG. 9 shows the results of an in-vivo experiment, comparing the biological response over a three weeks period of a single dose the protein erythropoietin administered subcutaneously, to the parenteral delivery of an identical dose of erythropoietin with a controlled-release device of the present invention. The sustained release of the protein was associated with greater biological activity at week 3, when compared to the subcutaneous administration.

EXAMPLE 3

Delivery of a Water-Insoluble Solute to Specific Sites

In one embodiment of the dispenser device, other solute or solutes can be added to the solute reservoir element to make possible or improve solubility of the target solute. The features of the dispenser that make it suitable for prolonged, linear release of solute into the environment also apply to the interior of the dispenser. That is, solutes within the reservoir are retained, compared to conventional formulations for which the solubilizing agent will rapidly diffuse away.

An example of the utility of the dispenser unit exists for the oral delivery of calcium salt(s) for the treatment of a variety of conditions, e.g., osteoporosis. The most widely employed calcium salt is calcium carbonate (containing 40% elemental calcium), which, however, is insoluble in aqueous medium unless the pH is less than about 5. Therefore, standard oral preparations of calcium carbonate depend upon acidification in the stomach for dissolution. For individuals lacking the ability to acidify stomach contents (e.g., those with pernicious anemia) cannot obtain calcium from these medications. Although normal individuals may be able to solubilize calcium carbonate in the stomach, practically no absorption takes place there (<2% of the total). Instead, absorption occurs mainly by a specific, saturable mechanism in the remaining length of gut, with decreasing rank of absorption ileum (60% of total), jejunum (20%), and colon. Thus, for a bolus of calcium solubilized in the stomach to be absorbed, calcium must remain uncomplexed with other moieties in the gut and be presented to a section of gut transporting below the maximum (saturated) rate.

To solubilize calcium and present it to sequential portions of the gut in a manner that minimizes the change of chelation or other inactivating reactions, a hybrid dispenser with a frustoconical gradient-forming element, and containing two solutes, is manufactured. Specifically, addition of ascorbic acid (or any other soluble acidifier) to a calcium carbonate load will, upon hydration, produce an low pH within the dispenser such that calcium carbonate goes into solution. During passage through the gut, continuous linear delivery of calcium will be provided from within the protected environment of the dispenser locally to each region of the gut capable of specific and non-specific absorption of calcium.

By way of another example, the calcium compound contained in the dispenser could be tribasic calcium phosphate, which has approximately the same content of elemental calcium as does calcium carbonate. By mixing powdered calcium phosphate and citric acid together in the molar proportions of 1:2 a mixture is produced which can be compressed into a hemispherical tablet under pressure. After applying a coating impermeable to water and providing a fenestration and gradient-forming element, calcium ions will be released without the production of effervescence, as does calcium carbonate.

Using the methods developed here, it will be immediately obvious to one practiced in the art how to design and manufacture various calcium dispensers. As a specific, but not limiting example, powdered calcium carbonate and ascorbic acid are mixed together in a 1:1 milliequivalent ratio, compressed in a hydraulic press into a hemisphere of radius 5 mm and subsequently covered with a mixture of cellulose acetate/PEG 600/acetone, with a 3 mm diameter source element, and a frustoconical gradient-forming element with a height of 1 mm and a release orifice of 1.5 mm.

EXAMPLE 4

Alternate Configurations of the Devices of the Invention

While the device depicted in three-dimensional form in FIG. 13 represents a preferred embodiment of the present invention, with a hemispherical solute reservoir element, a single opening forming a source element (not seen in this depiction) and a frustoconical gradient-forming element with a release orifice, many other alternate forms of the device are embraced by the teachings herein. Such examples are shown in FIGS. 10–12 and 14. In FIG. 10, the dispenser comprises the solute reservoir element, the source element (not visible in figure), and a gradient-forming element, but in this case, solute release is provided from a plurality of release orifices situated in a circumferential pattern along the portion of a tubular-shaped gradient-forming element proximal to the solute reservoir element. The device provides near zero-order rate release without an initial burst.

Figure 14:
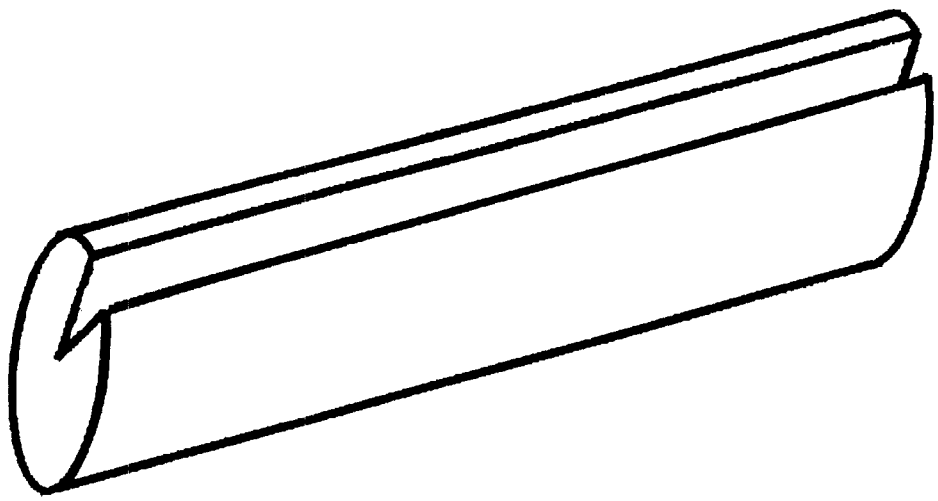
FIG. 14 shows a device of the invention suitable for parenteral administration, comprising a tubular-shaped solute reservoir element, an absent longitudinal sector providing the gradient-forming element, and a plurality of rows of openings therebetween being closer together at the center of the tubular element and becoming more distantly spaced towards to exterior, the openings forming the source element.
Figure 15:
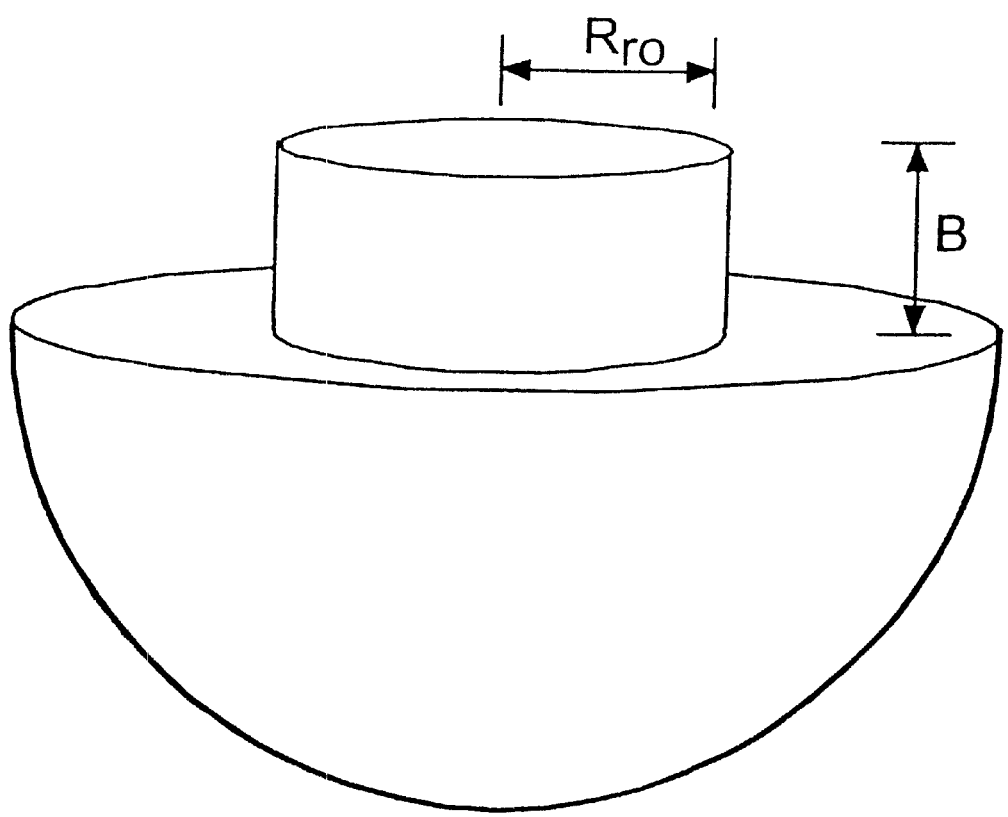
FIG. 15 depicts a device of the invention with a hemispherical solute reservoir element and a cylindrical gradient-forming element, and a circular release orifice.

In FIG. 11, a cube-shaped solute reservoir element is provided, with a gradient-forming element taking the form of a tubular cavity from the surface and formed part-way through the cube. The release orifice of the gradient-forming element is present at the surface of the cube where the cavity begins. The source element is provide by a plurality of circumferentially-oriented rings of orifices spaced closely together near the bottom of the cavity and the space between the rings of orifices widening as they approach the surface of the cube. In an alternate embodiment of the plural source element configuration, FIG. 12 represents a tubular solute reservoir element with three bore holes passing almost but not completely through the solute reservoir. The source elements comprise a series of circumferentially-oriented orifices as in FIG. 11, thus the three interfaces of the bore-holes with the solute reservoir element provide the release orifices of the device. In a further embodiment particularly suitable and useful for parenteral location and administration, FIG. 14 shows a tubular-shaped solute reservoir element with a longitudinal sector removed, the absent sector providing the gradient-forming element. The source element is provided by rows of orifices along the flat internal surfaces of the solute reservoir, the rows closely spaced towards the center and becoming more distantly spaced towards the exterior.

Figure 16:
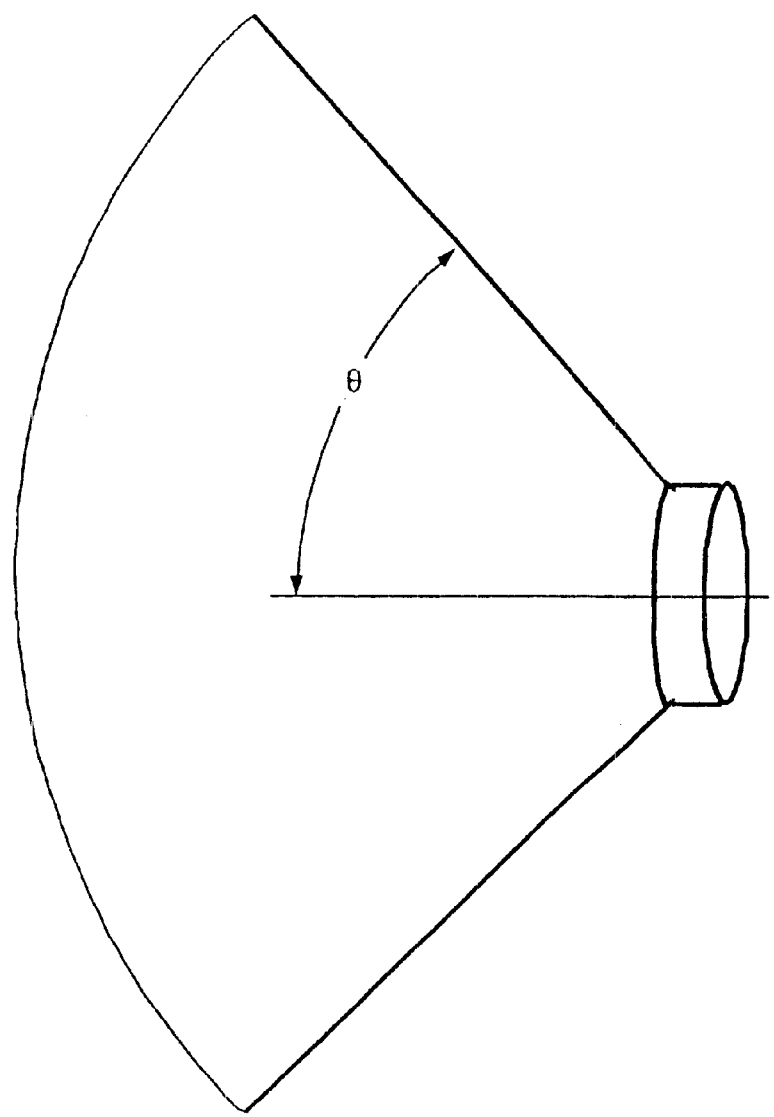
FIG. 16 depicts the general shape of another embodiment of the invention which comprises a frustoconical-shaped solute reservoir element and a cylindrical gradient-forming element.

In another embodiment of the invention, a dispenser may have a solute reservoir element in the shape of a truncated spherical cone and a gradient-forming element in the shape of a cylinder, as shown in FIG. 16.

Figure 17:
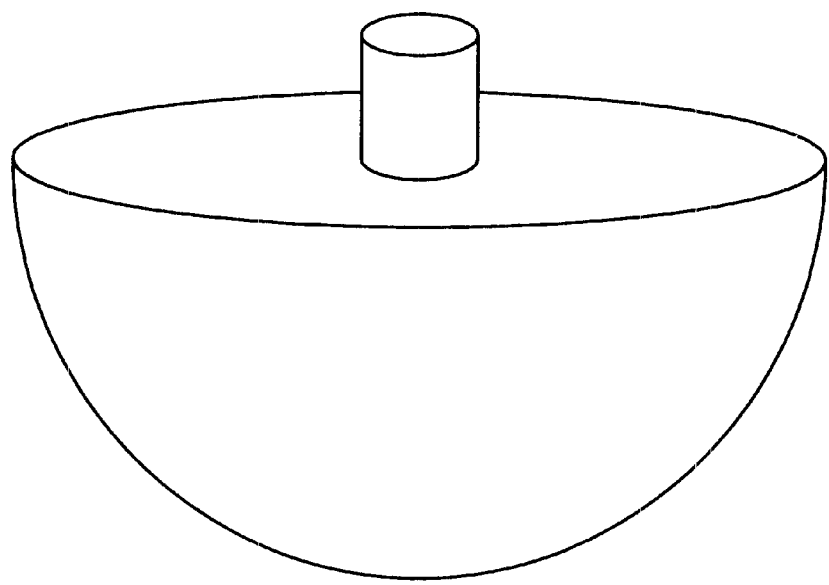
FIG. 17 depicts a capsule-shaped device comprising a hemispherical-shaped solute reservoir element with a cylindrical gradient-forming element continuous with the outer surface of the device.
Figure 18:
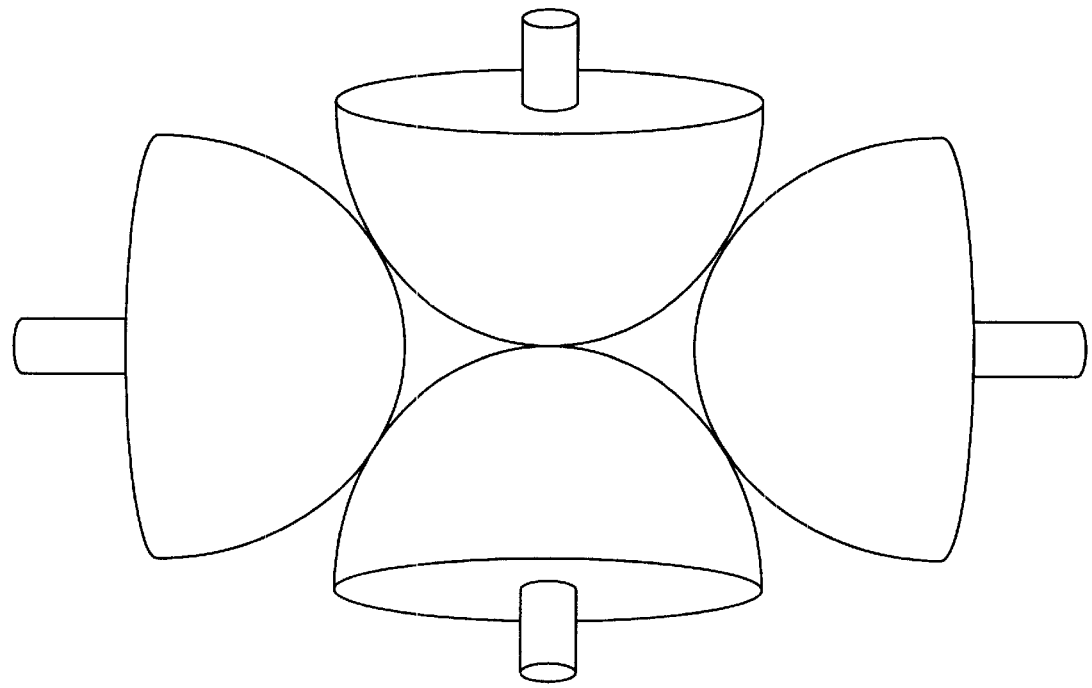
FIG. 18 illustrates how multiple dispensers with differing release kinetics can be incorporated into a single device so as to deliver solute in a manner unobtainable by a single dispenser.

As mentioned above, the final shape of the device of the invention may be tailored to the particular utility. For ease in swallowing, a dispenser may be provided in the shape of a capsule, such as shown in FIG. 17. The capsule comprises a dispenser with a hemispherical solute reservoir element and a cylindrical gradient-forming element. FIG. 18 shows a similar easy-to-swallow capsule containing four such dispensers, which in this case have different shapes and thus release characteristics: two have a short gradient-forming element and two have long such elements. All of the dispensers in a device may be the same, or some may be different, depending on the desired release parameters of the finished device. All of the aforementioned alternate embodiments of a device of the invention are merely illustrative of the variations in configuration of the combination of a solute reservoir element, one or more source elements, and one or more gradient-forming elements, each of the latter with one or more release orifices, to deliver one or more solvents with zero-order or near-zero-order rate release over time, without an initial release.

Figure 27:
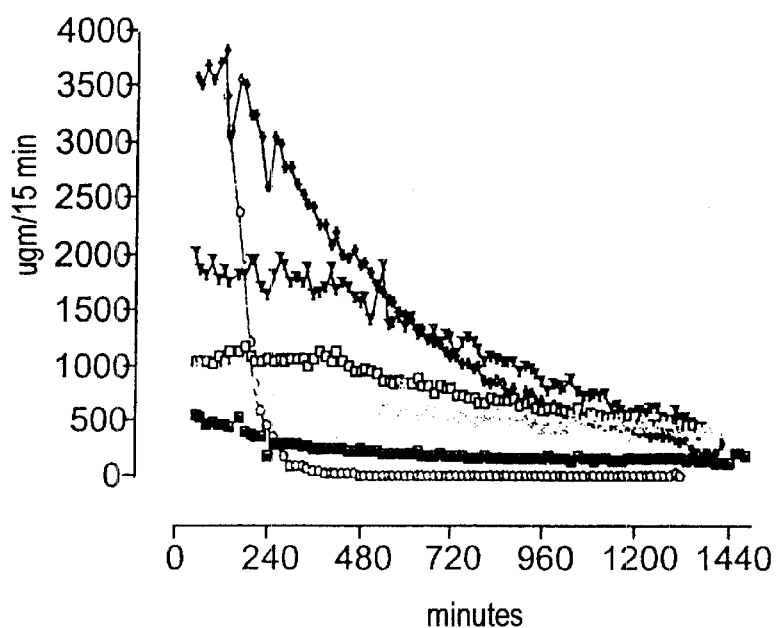
FIG. 27 depicts the release kinetics from up to 12 chloroquine-containing dispensers grouped together.

As mentioned above, the device of the invention may be adapted to hold one or more of the aforedescribed dispensers. For a device with a plurality of such exterior openings, each orifice associated with a release orifice of a dispenser, each exterior opening is at least three release-orifice-radii apart from another, preferably ten radii apart. FIG. 27 depicts the release kinetics from chloroquine-containing devices having up to 12 dispensers in a group, with decreasing distance among the release orifices with increasing numbers of dispensers. Each dispenser has a 1 mm high gradient-forming element, a 3 mm diameter release orifice and a total length of dispenser of 3 cm.

EXAMPLE 5

Figure 19:
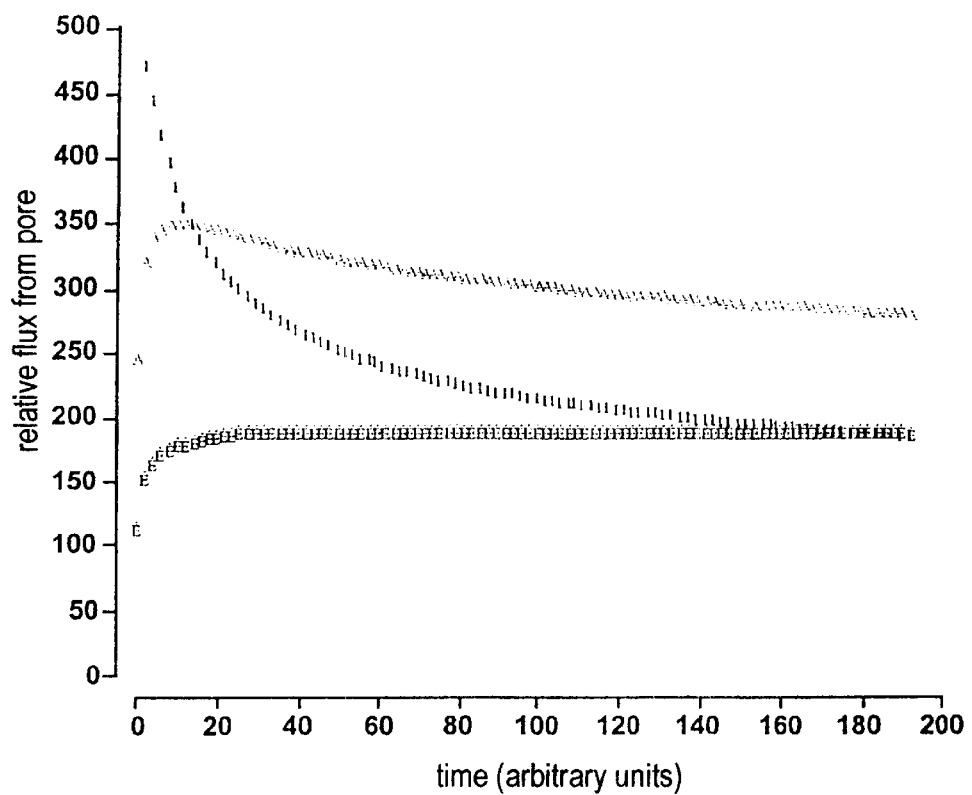
FIG. 19 compares theoretically the relative flux from a frustoconical device with no gradient-forming element, showing an initial burst and first-order release, as compared with identical devices but with cylindrical gradient-forming elements of ⅓, ⅐, and ¹⁄₁₅ the radius of the source element or release orifice. The devices with gradient-forming elements show no initial burst and near zero-order release.

FIG. 19 shows the theoretical modulation of initial release rates and time to reach steady state caused by cylindrical gradient-forming elements of different dimensions attached to identical truncated spherical cones as determined by numerical solution of the diffusion equation. A common truncated cone, one which was squat (i.e. ratio of base to tip greater than 1), and a fixed length of the gradient-forming element was used for each of the conditions plotted. The following parameters were evaluated: (1) a device without a gradient-forming element ("no gradient-forming element"); (2) a device with a gradient-forming element having a radius 1/3 that of the cone pore (1:3 gradient-forming element); (3) a device with a gradient-forming element of radius 1/7 the pore radius (1:7 gradient-forming element); and (4) a device having a gradient-forming element radius 1/15 that of the pore radius (1:15 gradient-forming element). The device without a gradient-forming element exhibits an initial rapid decay to a quasi-constant efflux rate for times >>200 arbitrary units. Addition of a gradient-forming element with a 1:3 ratio blunts the initial rapid decay but also increases the flux as well as its constancy. By selection of a 1:7 gradient-forming element relationship, not only can the initial rapid release phase be completely blunted, but in addition the efflux rate is now truly zero order. Decreasing the gradient-forming element radius further (e.g., 1:15) serves only to decrease further the rate of flux, which remains essentially constant. The exact relationships between these parameters, including the influence of the gradient-forming element height, are explored in an example below.

Figure 20:
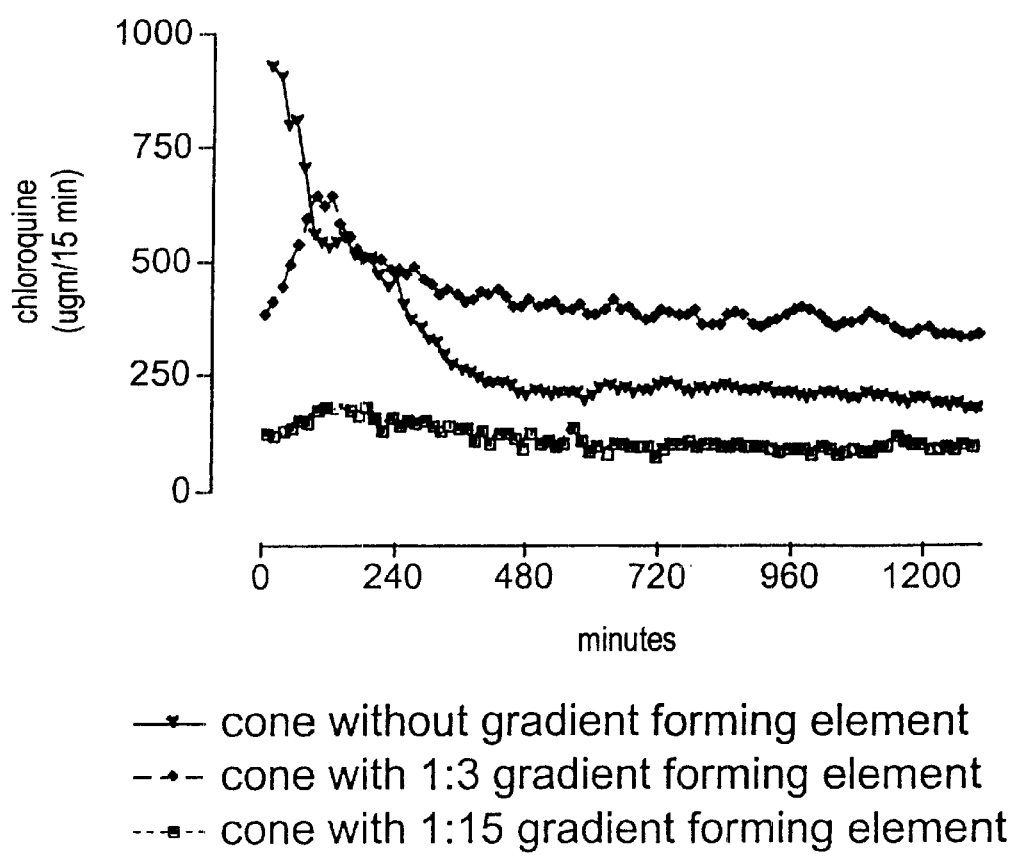
FIG. 20 illustrates the actual release of chloroquine from frustoconical devices constructed according to the theoretical calculations generated for FIG. 19. As experimentally verified for a 1:3 ratio, a cylindrical gradient-forming element will not only blunt the initial burst of release, but will also increase the delivery rate for prolonged periods of time compared to a dispenser lacking a gradient-forming element.

FIG. 20 illustrates the actual release of chloroquine from frustoconical devices constructed according to the theoretical calculations generated for FIG. 19. As experimentally verified for a 1:3 ratio, a gradient-forming element will not only blunt the initial burst of release, but will also increase the delivery duration compared to a dispenser lacking a gradient-forming element.

Figure 21:
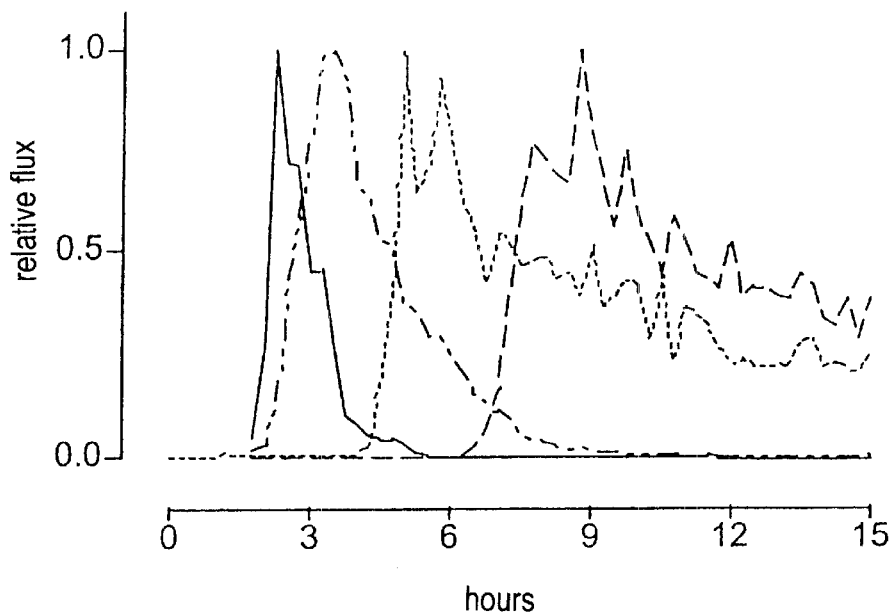
FIG. 21 illustrates that a frustoconical solute reservoir element with a cylindrical gradient-forming element can be designed to deliver chloroquine in a zero-order manner, in contrast to a frustoconical solute reservoir element alone which delivers with an initial burst, followed by a rapid exponential decay.
Figure 22:
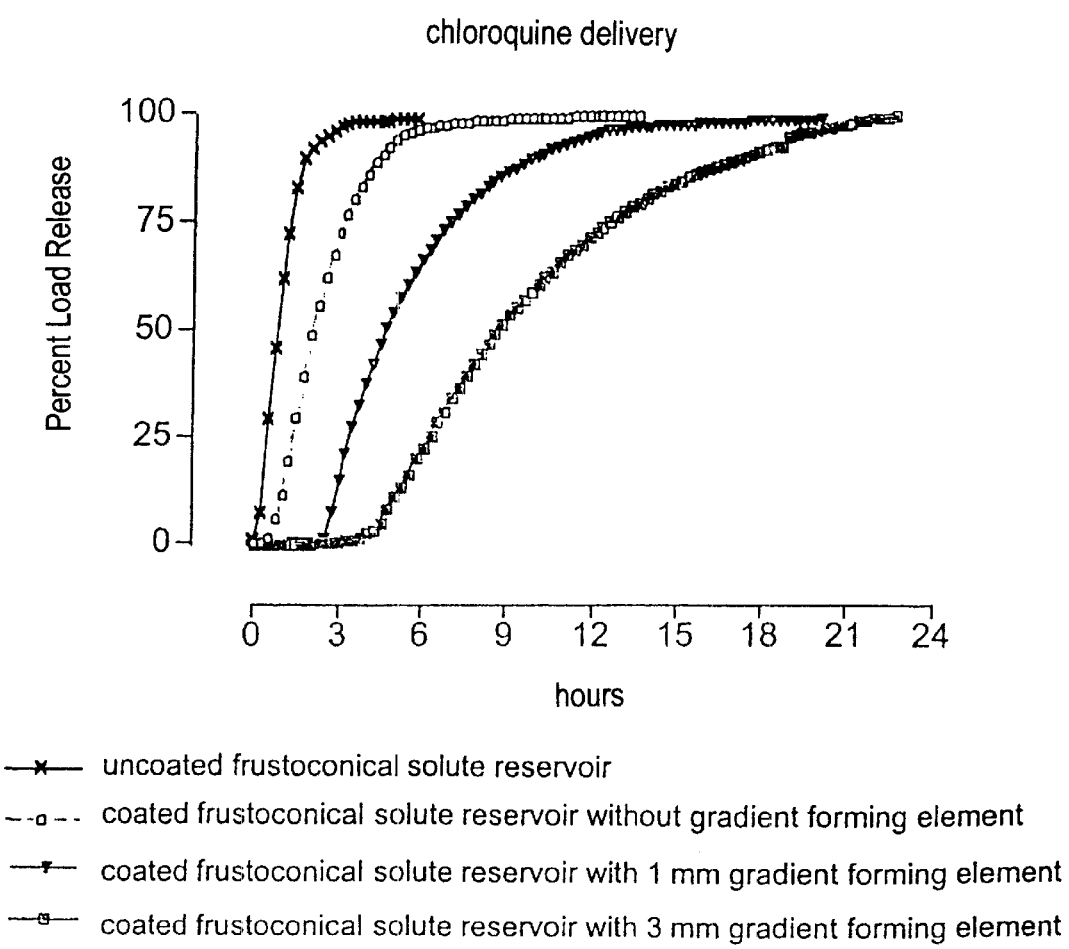
FIG. 22 illustrates the cumulative delivery of chloroquine by the devices depicted in FIG. 21.

FIG. 21 illustrates that a frustoconical device with a cylindrical gradient-forming element can be designed to deliver chloroquine in a zero-order manner at varying rates, in contrast to an identical but uncoated cone which delivers with an initial burst, followed by a rapid exponential decay, or a cone without a gradient-forming element. FIG. 22 shows the relative flux from frustoconical dispensers with cylindrical gradient-forming elements of 1 mm and 3 mm, compared to an uncoated dispenser and a coated dispenser without a gradient-forming element.

EXAMPLE 6

Exemplary Devices to Deliver Drugs Orally

Figure 23:
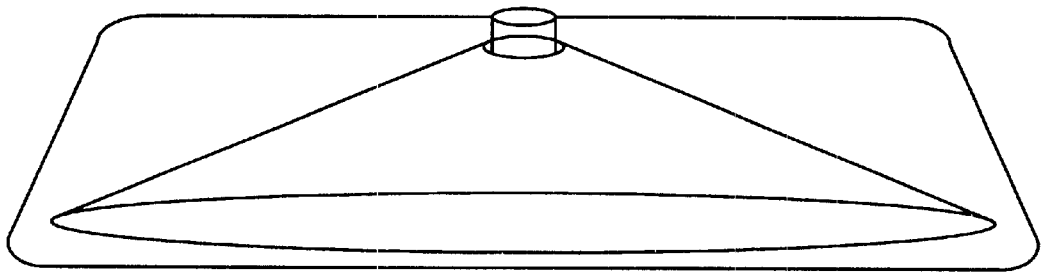
FIG. 23 illustrates a dispenser consisting of a frustoconical solute reservoir element and a cylindrical gradient-forming element designed for the sustained release of drug over 1 day when administered orally.
Figure 24:
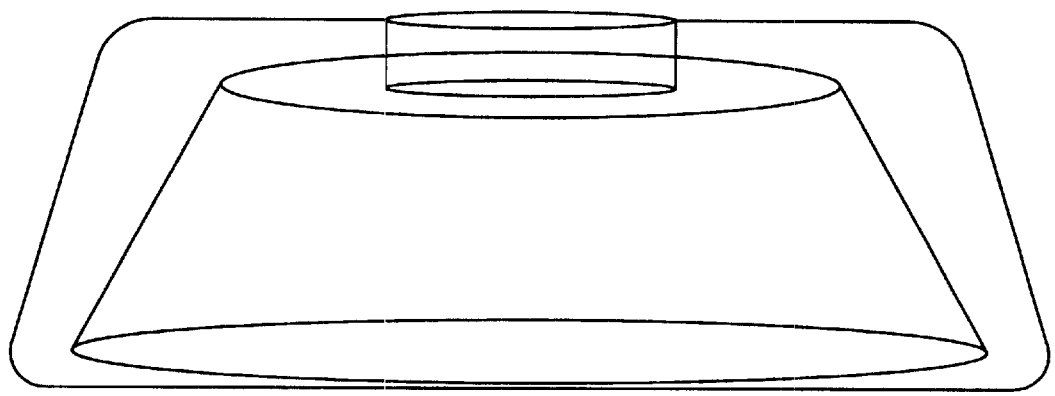
FIG. 24 illustrates what changes in geometry are necessary from the dispenser illustrated in FIG. 23 to deliver the load of drug in a sustained fashion over 2 days.
Figure 25:
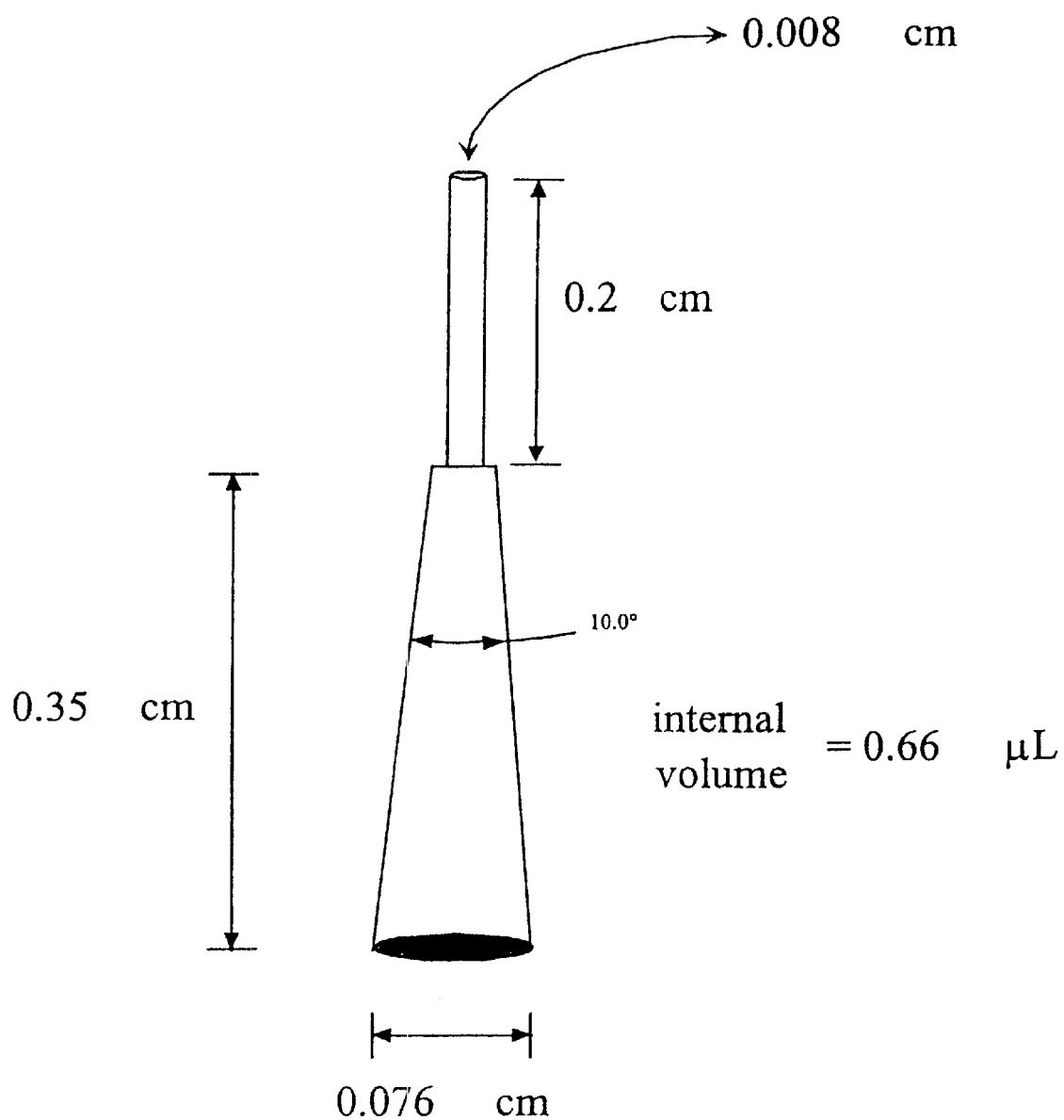
FIG. 25 illustrates one design for a parenteral device to deliver protein at a low, constant rate for about 30 days.

Design of a device to deliver solutes orally is typically constrained by the requirement for a nearly complete release of solute within the normal transit time in the gastrointestinal tract of patients; i.e., approximately 24 hrs. FIGS. 23 and 24 illustrate two different forms of a device to deliver chloroquine orally by constant release with a common feature of an identical base diameter. FIG. 24 corresponds to a moderately slender cone of vertex angle 25° ("thick device") whereas FIG. 23 corresponds to a wider cone of vertex angle 60° ("thin device"). Both assume a cylindrical gradient-forming element height of 0.01 cm. Using the flux equation given for frustoconical dispensers above for a load concentration of chloroquine at 500 mg/mL, and a diffusion coefficient of $5 \times 10^{-6}$, the parameters (shown in the table below) are selected to provide a release of 1.2 mg/hr for the thick device. The total load of chloroquine is ~49 mg, with ~29 mg being delivered over 24 hrs. In contrast, the thin device provides a smaller flux of ~670 microgram/hr, but releases ~16 mg of the load of ~16.5 mg. By modifying parameters in the flux equation, a practitioner of the art will be able to design straightforwardly a device to provide a specified profile of solute release.

Thin and Thick Device Characteristics

| VERTEX ANGLE ($2\theta$) | THIN DEVICE (120°) | THICK DEVICE (50°) |
|---|---|---|
| HEIGHT (H) | 0.22 cm | 0.815 cm |
| FRUSTUM (B) | 0.2 cm | 0.33 cm |
| TIP (T) | 0.02 cm | 0.487 cm |
| VOLUME | 33 µL | 97 µl |
| BASE RADIUS (R2) | 0.38 cm | 0.38 cm |
| RELEASE ORIFICE RADIUS (R1) | 0.034 cm | 0.226 cm |
| GRADIENT-FORMING ELEMENT RADIUS (Rc) | 0.03 cm | 0.06 cm |
| GRADIENT-FORMING ELEMENT LENGTH (Z) | 0.1 mm | 0.1 mm |
| [CHLOROQUINE] | 500,000 µg/mL | 500,000 µg/mL |

Exemplary Device to Deliver Drugs Parenterally.

Requirements for parenteral delivery of drugs include a shape for ease of insertion and generally a prolonged delivery duration compared to oral administration. These factors generally require a long, slender device profile. As an example, FIG. 27 illustrates one such device constructed to deliver the protein erythropoietin (MW ~34,000) at a rate of 20 units per day for a 30 day period. The parameters selected are tabulated below.

Parenteral Device Characteristics

| VERTEX ANGLE ($2\theta$) | 10° |
|---|---|
| HEIGHT (H) | 0.435 cm |
| FRUSTUM (B) | 0.35 cm |
| TIP (T) | 0.085 cm |
| VOLUME | 0.82 µL |
| BASE RADIUS (R2) | 0.038 cm (21.5 gauge) |
| RELEASE ORIFICE RADIUS (R1) | 0.015 cm |
| GRADIENT-FORMING ELEMENT RADIUS (Rc) | 0.004 cm |
| GRADIENT-FORMING ELEMENT LENGTH (Z) | 0.2 cm |
| [rhEPO] | $10^6$ U/mL (10 mg/mL) |
| Units/device | ~650 |
| output | 0.9 U/hr; ~20 U/day |
| Delivery duration | 30 days |

Many variations in construction will be apparent to those skilled in the art. For example, a high concentration of solute can be placed as a depot in the base of a dispenser which will provide a constant concentration over a long period of time.

EXAMPLE 7

Manufacture and Validation of a Truncated Cone with a Cylindrical Gradient-Forming Element for the Oral Delivery of Chloroquine Manufacturing of devices with a solute reservoir element having the shape of a truncated right circular cone and a gradient-forming element having the shape of a cylinder can be accomplished in many ways which will be evident to those skilled in the art. Processes can include, among others, molding, casting, extruding, or compression of solute with or without an excipient into the required geometrical shape and dimensions. Alternatively, powdered solute or solutes can be placed inside the shell of a dispenser with the solvent subsequently derived after administration from the external environment entering the cavity to initiate the process of diffusion. Wicking, such as the incorporation of fibers, wetting agents, or a hydrophilic matrix, etc. can be incorporated with the solute mixture within the device cavity and gradient-forming element to aid in filling the cavity with solvent. Further, other substances with specific purposes other than solute delivery can also be incorporated. For example, immunomodulating substances may be added to reduce local inflammatory response for implanted devices or buffering salts added to maintain the internal pH of the dispenser within a specific range.

Figure 26:
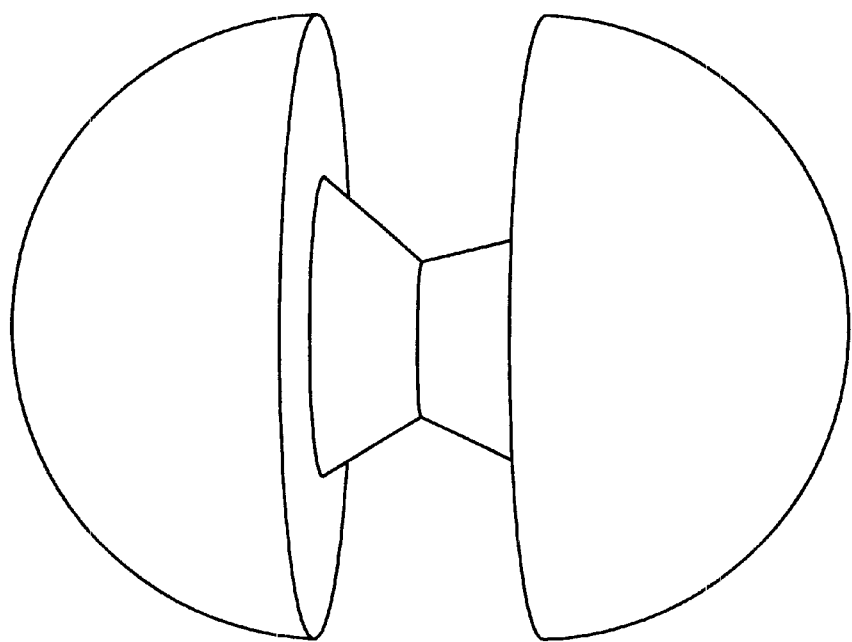
FIG. 26 shows an intermediate form in the process of the manufacture of a preferred embodiment of the invention.

Furthermore, the manufacture of a device having a solute reservoir element having the shape of a hemisphere and a gradient-forming element having the shape of a right truncated cone can be accomplished in many ways which will be evident to those skilled in the art. Processes can include, among others, molding, casting, extruding, or compression of solute with or without an excipient into the required geometrical shape and dimensions. In the example of an intermediate form during manufacture shown in FIG. 26, a symmetric dumbbell-shaped cast comprising two devices connected from release orifice to release orifice is prepared, and is then coated with impervious material. Cutting apart at the midpoint produces two identical dispensers. In an alternate embodiment, the dumbbell may be asymmetric to produce two types of dispensers with different characteristics.

References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing is from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A device for the continuous, linear, sustained release of one or more solutes comprising at least one dispenser, said dispenser comprising
   i) a solute reservoir element, said solute reservoir element defined by a fluid-impervious and solute-impervious wall and comprising a shape of a hemisphere, said hemisphere having a flat face, a center of said flat face, and a radius;
   ii) a source element in said wall, said source element consisting of a circular passageway at said center of said flat face of said hemisphere, said source element having a radius, said passageway allowing the diffusion of a solute from said solute reservoir element into a gradient-forming element;

iii) a gradient-forming element in fluid registry with said source element and into which said solute diffuses from said solute reservoir element, said gradient-forming element having a fluid-impervious and solute impervious wall and a shape of a truncated right circular cone with a base, a vertex, and a height from said base to said vertex;

iv) a release orifice defined by said vertex of said gradient-forming element for the diffusion of said solute from said dispenser, said release orifice having a radius;

wherein a ratio of said radius of said hemisphere to said radius of said source element is equal to or greater than about two, and said height of said gradient-forming element is equal to or less than about four times a ratio of said radius of said source element squared to said radius of said release orifice, and equal to or greater than about 0.1 times said ratio of said radius of said source element squared to said radius of said release orifice.

2. The device of claim 1 wherein a frustum of said cone has a vertex angle of between about 10° and about 135°.

3. The device of claim 2, wherein said vertex angle is about 60° to about 120°.

4. The device of claim 1, wherein said solute reservoir element is empty.

5. The device of claim 1, wherein said solute reservoir element contains a porous substrate.

6. The device of claim 1, wherein said device has a shape selected from the group consisting of cone, cylinder, sphere, ellipse, hemisphere, capsule rod, needle, and sheet.

7. The device of claim 1, wherein said solute reservoir element contains a solute at an initial concentration $C_o$, said radius of said solute reservoir element is $R_{sr}$, said source element with radius $R_{se}$, said solute having a diffusion coefficient D, said vertex angle of said gradient-forming element is 2θ, said solute has a release rate from said release orifice, said release orifice has a radius $R_{ro}$, said release rate is given by:

$$i = \frac{\pi R_{ro} R_{se} D C_0}{\frac{(R_{se} - R_{sr})R_{ro}}{R_{sr}2} + \frac{\pi R_{se}}{4} + \frac{\tan\theta(R_{se} - R_{ro})}{2(1 - \cos\theta)}}$$

wherein i is said rate of solute flux from said release orifice at steady state.

8. The device of claim 1, wherein said release orifice is coated with a material that is soluble under preselected conditions.

9. The device of claim 8, wherein said material is soluble at a preselected pH.

10. The device of claim 1, wherein said one or more solutes is a therapeutic agent.

11. The device of claim 10 wherein said therapeutic agent is selected from the group consisting of a calcium salt, parathyroid hormone, antihypertensive agents, diuretics, sympatholytic drugs, vasodilators, calcium channel blockers, analgesics, opioids, non-steroidal anti-inflammatory agents, antihistamines, antidepressants, hypnotics, sedatives, antiepileptic agents, antiarrhythmic agents, antiparasitic agents, antimicrobial agents, chloroquine, anti-Parkinson agents, antineoplastic agents, contraceptives, hypoglycemics, electrolytes, vitamins, minerals, nutriceuticals, local anesthetics, diagnostic agents, peptide growth factors, hormones, cytokines, stimulants, amphetamine, methylphenidate, antianxiety agents, benzodiazepines, hematopoietic agents, erythropoietin, stem cell factor, interleukins, and mixtures thereof.

12. The device of claim 1, wherein said one or more solutes is an erythropoietin.

13. The device of claim 1, wherein said one or more solutes is chloroquine.

14. The device of claim 1, wherein said one or more solutes is dissolved in a solvent or pharmaceutically acceptable vehicle.

15. The device of claim 1, wherein said one or more solutes is dry.

16. The device of claim 1, wherein said one or more solutes is not water soluble.

17. The device of claim 1 which contains a solute-modifying agent.

18. The device of claim 1 wherein said ratio of said radius of said hemisphere to said radius of said source element is equal to or greater than about 5.

19. The device of claim 18 wherein said ratio is equal to or greater than about ten.

20. The device of claim 1 wherein said height of said gradient-forming element is equal to or less than about two times a ratio of said radius of said source element squared to said radius of said release orifice.

21. A method for delivering one or more solutes in a linear, sustained release fashion, comprising administering to a desired site of delivery at least one device in accordance with claim 1.

22. The method of claim 21, wherein said one or more solutes is delivered to the body of an animal, said one or more solutes delivered orally, sub-lingually, rectally, vaginally, sub-dermally, intramuscularly, ocularly, topically, nasally, aurically, intravenously, or into a particular anatomical location.

23. A kit comprising at least one device for the continuous, linear, sustained release of one or more solutes comprising at least one dispenser, said dispenser comprising i) a solute reservoir element, said solute reservoir element defined by a fluid-impervious and solute-impervious wall and comprising a shape of a hemisphere, said hemisphere having a flat face, a center of said flat face, and a radius;

ii) a source element in said wall, said source element consisting of a circular passageway at said center of said flat face of said hemisphere, said source element having a radius, said passageway allowing the diffusion of a solute from said solute reservoir element into a gradient-forming element;

iii) a gradient-forming element in fluid registry with said source element and into which said solute diffuses from said solute reservoir element, said gradient-forming element having a fluid-impervious and solute impervious wall and a shape of a truncated right circular cone with a base, a vertex, and a height from said base to said vertex;

iv) a release orifice defined by said vertex of said gradient-forming element for the diffusion of said solute from said dispenser, said release orifice having a radius;

wherein a ratio of said radius of said hemisphere to said radius of said source element is equal to or greater than about two, and said height of said gradient-forming element is equal to or less than about four times a ratio of said radius of said source element squared to said radius of said release orifice, and equal to or greater than about 0.1 times said ratio of said radius of said source element squared to said radius of said release orifice.

24. A device for the continuous, linear, sustained release of one or more solutes comprising at least one dispenser, said dispenser comprising
  i) a solute reservoir element, said solute reservoir element defined by a fluid-impervious and solute-impervious wall and comprising a shape of a hemisphere, said hemisphere having a flat face, a center of said flat face, and a radius
  ii) a source element in said wall, said source element consisting of a circular passageway at said center of said flat face of said hemisphere, said source element having a radius, said passageway allowing the diffusion of a solute from said solute reservoir element into a gradient-forming element;
  iii) a gradient-modifying element in fluid registry with said source element and into which said solute diffuses from said solute reservoir element, said gradient-forming element having a fluid-impervious and solute impervious wall, said gradient-forming element having the shape of a cylinder, said cylinder having a radius, an end in fluid registry with said source element, a height, and an other end;
  iv) a release orifice defined by said other end of said cylinder for the diffusion of said solute from said dispenser;

wherein a ratio of said radius of said hemisphere to said radius of said source element is equal to or greater than about two, and said height of said gradient-forming element is equal to or less than about four times the radius of said gradient-forming element, and said height of said gradient-forming element is greater than about 0.1 times said radius of said gradient-forming element.

25. The device of claim 24 wherein said radius of said hemisphere comprising the maximum internal diffusion surface is equal to or greater than about five times the radius of said cylinder.

26. The device of claim 24 wherein said radius of said hemisphere comprising the maximum internal diffusion surface is equal to or greater than about ten times said radius of said cylinder.

27. The device of claim 24 wherein said height of said cylinder is equal to or less than about two times said radius.

28. A method for delivering one or more solutes in a linear, sustained release fashion, comprising administering to a desired site of delivery at least one device in accordance with claim 24.

29. A kit comprising at least one device in accordance with claim 24.

* * * * *